(12) United States Patent
Middeldorp et al.

(10) Patent No.: US 6,936,251 B2
(45) Date of Patent: Aug. 30, 2005

(54) PEPTIDE REAGENT FOR THE DETECTION OF HUMAN CYTOMEGALOVIRUS (CMV)

(75) Inventors: Jaap Michiel Middeldorp, Oss (NL); Johannes Martinus Gerardus Van De Crommert, Veghel (NL)

(73) Assignee: bioMerieux, B.V., Boxtal (NL)

( * ) Notice: Subject to any disclaimer, the term of this patent is extended or adjusted under 35 U.S.C. 154(b) by 0 days.

(21) Appl. No.: 10/288,220

(22) Filed: Nov. 5, 2002

(65) Prior Publication Data

US 2003/0119039 A1 Jun. 26, 2003

Related U.S. Application Data

(63) Continuation of application No. 09/214,806, filed as application No. PCT/EP97/03717 on Jul. 9, 1997, now abandoned.

(30) Foreign Application Priority Data

Jul. 12, 1996 (EP) .............................................. 96201972

(51) Int. Cl.[7] ........................ A61K 38/00; C07K 14/00; C07K 14/005; C07K 14/045; G01N 33/53
(52) U.S. Cl. ............................... 424/186.1; 424/184.1; 424/185.1; 424/204.1; 424/230.1; 435/4; 435/5; 435/7.1; 530/300; 530/350
(58) Field of Search .......................... 424/144.1, 185.1, 424/186.1, 192.1, 204.1, 229.1, 230.1, 184.1; 435/4, 5, 7.1, 7.6, 7.9, 7.92, 69.1, 69.3, 320.1, 235.1, 69.2, 71.1; 436/518, 531, 532, 351; 514/2, 8; 530/300, 350, 387.1, 389.3, 389.4, 395, 403, 324, 326, 327, 328, 388.3; 536/23.1, 27.72

(56) References Cited

U.S. PATENT DOCUMENTS

| 5,744,298 A | 4/1998 | Stuber et al. |
| 5,859,185 A | 1/1999 | Stuber et al. |
| 6,120,989 A | 9/2000 | Vornhagen et al. |

FOREIGN PATENT DOCUMENTS

| DE | 3619902 | 3/1988 |
| DE | 4128684 | 4/1993 |
| DE | 4426453 | 11/1995 |
| EP | 236145 | 9/1987 |
| EP | 0 248 909 A1 | 12/1987 |
| EP | 0 330 051 A1 | 8/1989 |
| WO | WO 92/00323 | 1/1992 |

OTHER PUBLICATIONS

Ayata et al., Journal of General Virology, vol. 43, pp. 380–392 (1994).*
NCBI printout of Accession P06473, Glycoprotein B precursor (Jan 1988).*
NCBI printout of Accession P13200, 28 KD Structural Phosphoprotein (Jan 1990).*
Sundqvist et al., Journal of Clinical Microbiology, vol. 30, No. 10, pp. 2735–2739 (Oct 1992).*
NCBI printout of Accession P08318, Large Structural Phosphoprotein (PP150) . . . (Aug 1988).*
Ripalti et al., Journal of Clinical Microbiology, vol. 32, No. 2, pp. 358–363 (Feb 1994).*
Landini et al., Journal of Clinical Microbiology, vol. 29, No. 9, pp. 1863–1872 (Sept 1991).*
Giugni et al. 1992. Journal of Virology 73:2367–2374.
Marshall et al. 1994. Journal of Medical Virology 43:77–83.
Meyer et al. Sep. 1989. Database PIR 68, Accession No. WMBE28.
Shiu et al. Feb. 1995. Database PIR 68, Accession No. S40226.
Ayata et al. "Different Antibody Response to a Neutralizing Epitope of Human Cytomegalovirus Glycoprotein B Among Seropositive Individuals" *Journal of Medical Virology* 43:386–392 (1994).
Greijer et al. "Molecular Fine–Specificity Analysis of Antibody Responses to Human Cytomegalovirus and Design of Novel Synthetic–Peptide–Based Serodiagnostic Assays" *Journal of Clinical Microbiology* 37(1):179–188 (1999).
International Search Report corresponding to PCT/EP 97/03717 mailed on Nov. 14, 1997.
Van Zanten et al. "Comparative Immunoblot Analysis with Ten Different, Partially Overlapping Recombinant Fusion Proteins Derived From Five Different Cytomegalovirus Proteins" *Microbiologica* 18:223–228 (1995).

* cited by examiner

*Primary Examiner*—James Housel
*Assistant Examiner*—Zachariah Lucas
(74) *Attorney, Agent, or Firm*—Myers, Bigel, Sibley & Sajovec, P.A.

(57) ABSTRACT

The invention relates to a peptide reagent comprising peptides immunochemically reactive with antibodies to the human cytomegalovirus (CMV). New antibodies directed to said peptides or fragments thereof are also part of the invention. Also cell lines capable of producing monoclonal antibodies are part of the invention. The invention also relates to a method for the detection of CMV or antibodies directed against CMV in a test fluid and a test kit to be used when applying the said detection methods. Detection of CMV in a test fluid or tissue specimen using antibodies, monoclonal and polyclonal, directed to said peptide, which have the characteristics of detecting both native and denatured DMV proteins are also part of said invention.

6 Claims, 20 Drawing Sheets

Immuno-staining samples on CMV-blot

Stripno. 1: Humane serum CMV IgG positive
Stripno. 2: CMV.OT3C Moab against CMV-pp150
Stripno. 3: GICR 1201 Moab against CMV-pp28
Stripno. 4: GICR 1202 Moab against CMV-pp52
Stripno. 5: GICR 1205 Moab against CMV-pp65

PEPTIDE REAGENT FOR THE DETECTION OF HUMAN CYTOMEGALOVIRUS (CMV)

RELATED APPLICATION INFORMATION

This application is a continuation application of U.S. application Ser. No. 09/214,806, filed Feb. 4, 1999 now abandoned, which claims the benefit under 35 U.S.C. § 371 from PCT Application No. PCT/EP97/03717, filed Jul. 9, 1997, which claims the benefit of European Application Serial No. 96201972.5, filed Jul. 12, 1996; the disclosures of which applications are incorporated by reference herein in their entireties.

FIELD OF THE INVENTION

The present invention relates to a peptide reagent comprising peptides immunochemically reactive with antibodies to the human cytomegalovirus (CMV), (monoclonal) antibodies directed against said peptides, and cell lines capable of producing monoclonal antibodies. The invention is further concerned with methods for (direct) detection of CMV or (indirect) detection of antibodies directed against CMV.

BACKGROUND OF THE INVENTION

Cytomegalovirus (CMV) is a member of the human herpesvirus family, infecting between 50–100% of all individuals worldwide depending on age and socio-economic status.

CMV is naturally transmitted via saliva, urine or breast milk but can also be recovered from other body secretions. In addition, CMV can be transmitted transplacentally to the foetus, by geno-urinary contact during birth or intercourse, by blood transfusion (esp. white cells) and bone marrow cq. organ transplant.

After primary infection CMV persists in the body for the lifetime of its host in a state of dynamic latency, well controlled by the host immune system, and may be recovered periodically from different sites and body secretions.

Although generally benign, CMV infections can be devastating and fatal in individuals with immune defects, such as transplant recipients, AIDS patients, patients with genetically determined immunodeficiencies and newborns with an immature immune system.

Therapeutic intervention is possible using drugs affecting viral DNA replication but this is associated with significant toxicity. Modulation of host immunity is another effective way of controlling CMV infection, which can be achieved by vaccination, passive immunotherapy using immunoglobulins or T-cells, or by manipulation of immunosuppressive therapy.

Identification and monitoring of active (symptomatic) infection due to CMV cannot be done based upon clinical parameters alone, as these are diverse and variable, or by manipulation of immunosuppressive therapy.

Identification and monitoring of active (symptomatic) infection due to CMV cannot be done based upon clinical parameters alone, as these are diverse and variable, but heavily depends on rapid and accurate laboratory diagnosis.

CMV-specific diagnosis can be achieved by a variety of techniques directly detecting viral components or indirectly measuring changes in the hosts immune status. Reliable diagnostic approaches require sensitive and reproducible technology based upon well defined and highly CMV-specific reagents and a detailed understanding of the molecular processes underlying CMV-infection in the human host.

CMV is the largest and most complex of the human herpesvirinae, with a genome of 230–270 kilobases.

Characteristic for a herpesvirus, the structural components of the CMV virion include a protein-DNA core, an icosahedral capsid consisting of 162 capsomer subunits, an amorphous layer of proteins called tegument and a surrounding proteo-lipid envelope essential for virus infectivity.

Although in vivo CMV can be found in a variety of host cells and tissues, with different levels of viral gene expression, efficient gene expression and viral DNA replication in vitro is only possible in primary fibroblast cells of human origin. Therefore this system has been most widely used to study viral gene expression, replication and characterization of related protein products.

Following binding, de-envelopment and penetration into a susceptible host cell (e.g. human fibroblast), tegument proteins from the incoming virion activate the expression of viral genes of the immediate early (IEA) class, encoding a limited number of protein species with broad-acting transcriptional activating functions, capable of transactivating the transcription of a wide variety of viral and host genes. Viral genes activated by IEA products predominantly consist of enzymes involved in nucleotide metabolism and DNA synthesis and are classified as the group of early antigens (EA). In the last stage of infection and essentially depending on the synthesis of new viral DNA templates by the virally encoded DNA polymerase (an EA component), a third (late antigen (LA)) group of viral proteins is expressed, consisting of the structural components required for assembly and release of viral progeny.

Both in vivo and in vitro, this sequence of gene expression can be interrupted at various stages leading to non-lytic (abortive or defective) infection cq. persistence, which is characterized by restricted gene expression patterns. These patterns are both dependent on the type of cell infected and on its activation and differentiation status. Viral gene products thus expressed still may alter host cell characteristics resulting in aberrant behavior and function.

In addition to the expression of its own genes in a 3-step cascade regulated fashion, CMV stimulates host cell gene expression following infection, thus complicating the specific analysis and purification of viral products.

In blood, CMV can be found in sporadic monocyte/macrophages (replicating), lymphocytes (abortive/restricted), polymorph nuclear cells (only PP65 protein) and circulating endothelial cells (replicating). Furthermore CMV can be detected in smooth muscle cells lining the arteries and smaller blood vessels (restricted/lytic) and fibroblast and macrophage-like cells in a variety of tissues.

In the absence of effective immune responses CMV can spread to virtually any tissue and cell type in the body.

The presence of infectious virus in the blood as determined by culture techniques is considered the best marker associated with active symptomatic infection, whereas the presence of viral DNA is a marker for virus carrier status.

CMV is associated with a wide variety of disease syndromes both in the immunocompetent and in the immunocompromised host, although the latter are much more frequent and associated with significantly greater morbidity and mortality.

Primary infection in the immunocompetent host usually go unnoticed. However CMV is considered to be causing 10% of the mononucleosis syndrome in adolescents and young adults and is frequently associated with acute nonA–G hepatitis. Primary infection in pregnant women is associated with the transplacental transfer of CMV to the foetus.

CMV is the leading cause of birth defects in the world, infecting between 0.5 and 3% of all newborns. In about 10% of infected newborns CMV-related defects can be detected, which are most serious in case of a primary infection in the mother.

CMV is named the "Troll of transplantation: as it is the most frequent infectious cause of complications in solid organ and bone marrow transplant recipients.

CMV also is a leading cause of disease in HIV positives and AIDS patients, most frequently associated with pneumonia, retinitis and gastrointestinal complications.

Finally, CMV frequently causes disease in patients with genetically determined immunodeficiencies, cancer patients and patients with autoimmune diseases.

The quality of the host immune status determines the balance between CMV replication and spread and viral persistence in a dormant latency state.

Host immune responses are induced and maintained upon encounter of newly synthesized or stable persisting viral gene products expressed during the different stages of infection at various sites/tissues in the body.

Depending on the virus-host interactions at the molecular level—which may be different for each individual—immune responses are built up gradually following primary infection until a state of balance is achieved, which is called latency.

Determination of the quality and quantity of host immune responses to CMV are of diagnostic and prognostic importance and have been widely used to determine immune status to CMV, to establish the donor/recipient CMV carrier status in the transplant setting and to identify/monitor acute infections in a variety of CMV-associated disease syndromes.

Diagnostic assays may directly measure the presence and quantity of virus in body fluids, by means of virus culture or DNA detection/quantitation techniques. However, only CMV detection in the blood is considered as a reliable parameter for diagnosis of active infection in man, as the virus may be secreted intermittently in urine and saliva in most healthy CMV carriers.

DNA detection in blood is not considered a reliable predictor for active CMV infection as latently infected CMV DNA positive leukocytes can be detected in most if not all healthy carriers, depending on the sensitivity of the assay used.

Measurement of CMV RNA expression in blood leukocytes may be useful for detecting active virus replication in the blood depending on the genomic target sequence analyzed.

Alternatively the antigenaemia assay, i.e. the quantitation of blood leukocytes (esp. polymorph nuclear cells) for the presence of intracellular PP65(UL83), has proven to be a reliable diagnostic parameter correlating well with active and symptomatic CMV infection in a variety of CMV disease syndromes.

In contrast to methods for the direct detection of virus or viral products, the analysis of humoral immune responses to CMV can be used as an indirect reflection of CMV activity in the human host. CMV serology is probably the most widely used approach for the diagnosis and monitoring of active CMV infections and for determination of CMV carrier status. A wide variety of techniques are available which are both rapid and cheap for detecting IgM, IgG or IgA antibodies to CMV.

Whereas the detection of CMV IgM and to a lesser extent CMV IgA is directly indicative for (recent) active infection, especially during a primary infection, the measurement of CMV IgG may be applied both for determination of CMV carrier status and for diagnosing/monitoring CMV disease.

During primary infection IgG antibodies are formed rapidly and remain present for life. Besides the presence of CMV IgM a significant rise in CMV IgG is reflecting active infection in the host. The latter may be complicated in case of full blood transfusion or immunoglobulin therapy.

Besides being a measure of active infection the generation of an antibody response to CMV is a reflection of immunocompetence and can be used to guide antiviral therapy in the immunocompromised. Detection of a brisk antibody response during antiviral therapy may be used as a sign to end the therapy and to allow the immune system to take over the control of CMV in the host.

Thus, serology is a reliable and versatile tool in the diagnosis and monitoring of CMV infections in the human host.

In the design of serological assays a crucial ingredient is the CMV-specific antigen preparation which serves to bind immunoglobulins in the sample to be analyzed. Thus it is important to define the fine molecular specificity of anti-CMV antibody responses in order to allow standardization. Such studies have been initiated in recent years but have proven difficult due to the diversity of anti-CMV antibody responses and the complexity of the CMV system.

Although the 235KB CMV genome of prototype strain AD169 has been sequenced completely and over 200 potential protein encoding open reading frames have been identified, only some 40 of these proteins have been biochemically and immunologically studied to date. A limited number of CMV polypeptides have been defined as targets for human antibody responses, such as pp150 (UL32), pp72(UL122/123), pp65(UL83), pp52(UL44), pp38(UL80), pp28(UL99), gB(UL55) and MDBP(UL57). Additional immunoreactive polypeptides have been defined by their molecular weight in CMV-infected cell extracts analyzed using the immunoblot technique, but their coding frames on the CMV genome have not been defined yet.

As stated above many different techniques are currently used for CMV serology.

These methods either use cell culture derived (semi-purified) antigen extracts, partially purified extracellular vinons and dense bodies or more defined (recombinant) proteins and fragments thereof. Due to this variation of methodology and lack of uniform and well defined reagents, CMV serology currently is not well standardized. Reliable diagnosis and further standardization of CMV serology therefore calls for the use of molecular defined and highly purified CMV antigens.

Such antigens may be produced and purified from CMV cell culture, but this is expensive and complicated by the presence of a multitude of host cell proteins. Recombinant CMV proteins expressed in alternative host systems require even higher grade of purification as patient sera may have antibodies to such host cell components leading to potential false positive results.

An example of the use of recombinant proteins can be found in Patent Application WO 95/00073, wherein a mixture of recombinant antigens (fusion proteins) are used to detect CMV specific IgM.

Synthetic peptides represent a highly defined alternative for such protein antigens and can be produced and purified in a highly reproducible manner.

SUMMARY OF THE INVENTION

It is an object of this invention to define an optimal combination of synthetic peptide reagents that are specifically suited for application in CMV serological techniques as they are highly reactive with human serum immunoglobulins of both the IgG and IgM class.

These reagents can be synthesized highly reproducibly and are easily purified, and thus are well suited for further improvement and standardization of CMV serology.

Antibodies to these peptide reagents may be useful in the development and quality control of serologic assays and for the direct detection of CMV.

Defining synthetic peptide fragments, representing immunodominant domains of CMV proteins, capable of replacing the intact proteins in diagnostic tests, is a subject of the present invention.

Synthetic peptides have the advantage of being chemically well defined, thus allowing easy and reproducible production at high yields, well suited for application in diagnostic assays which can be manufactured and used with greater reproducibility.

DETAILED DESCRIPTION OF THE INVENTION

The present invention provides a peptide reagent for the detection of antibodies to the Cytomegalovirus, wherein said reagent comprises a peptide derived from the Cytomegalovirus structural phosphoprotein pp150 (UL32) and a peptide derived from one of the Cytomegalovirus proteins pp52 (UL44), pp28 (UL99), or gB (UL55).

Furthermore, the present invention provides a peptide reagent comprising a peptide derived from CMV pp 150 protein comprising at least part of the amino acid sequence as shown in SEQ.ID.NO.: 1–6.

A preferred embodiment of the present invention is a peptide reagent comprising a peptide derived from pp150 protein comprising at least part of the amino acid sequence as shown in SEQ.ID.NO.: 1.

A further object of the present invention is a peptide reagent comprising a peptide from CMV gB protein comprising at least part of the amino acid sequence as shown in SEQ.ID.No.: 7.

Another object of the present invention is a peptide reagent comprising a peptide from CMV pp52 protein comprising at least part of the amino acid sequence as shown in SEQ.ID.No.: 8.

Another object of the present invention is a peptide reagent comprising a peptide from CMV pp28 protein comprising at least part of the amino acid sequence as shown in SEQ.ID.No.: 10.

A preferred embodiment of the present invention is a peptide reagent comprising a peptide having the amino acid sequence as shown in SEQ ID No.: 10.

A most preferred embodiment of the present invention is a peptide reagent comprising a peptide having the amino acid sequence as shown in SEQ ID No.: 1, a peptide having the amino acid sequence as shown in SEQ ID No.: 7 and a peptide having the amino acid sequence shown in SEQ.ID.No.: 10.

Another most preferred embodiment of the present invention is a peptide reagent comprising a peptide having a amino acid sequence as shown in SEQ ID No.: 1 and a peptide having the amino acid sequence shown in SEQ.ID.No.: 8.

In contrast to the natural CMV, the peptides according to the invention have the great advantage that these are of a safe non-infectious origin.

The peptides and fragments thereof which are preferably used in a peptide reagent according to the invention are found to be particularly suitable for use in a diagnostic method for the determination of the presence of CMV or CMV antibodies in a sample. Moreover, said peptides and fragments thereof may be used in suitable pharmaceutical dosage forms in the treatment of a CMV-related disease. The preparation of vaccines thus obtained which contain a peptide or fragment thereof as active ingredients, is known to one skilled in the art.

The peptides which are preferably used in a peptide reagent according to the present invention have improved reactivity and specificity (performance) compared with currently available CMV reagents.

Therefore the utilization of these immunological reagents in serological tests allows the development of assays that will permit a better differential diagnosis in patients with active CMV infections.

Furthermore, another object of the present invention is the finding that the presence of antibodies to the selected CMV peptides is correlated with active CMV infection.

The term "peptide reagent" as used herein refers to one or more peptides and a suitable support or a labeling substance.

Supports which can be used are, for example, the inner wall of a microtest well or a cuvette, a tube or capillary, a membrane, filter, test strip or the surface of a particle such as, for example, a latex particle, an aldehyde particle (such as a ceramic magnetizable particle with active aldehyde surface groups), an erythrocyte, a dye sol, a metal sol or metal compound as sol particle, a carrier protein such as BSA or KLH.

Labeling substances which can be used are, inter alia, a radioactive isotope, a fluorescent compound, an enzyme, a dye sol, metal sol or metal compound as sol particle.

In a method for the detection of antibodies directed against CMV in a sample, an peptide reagent according to the invention is brought into contact with the sample. After which, the presence of immune complexes formed between the peptide and antibodies in the sample is detected and by this detection the presence of CMV antibodies in the sample is known and can be determined quantitatively.

Depending on the nature and further characteristics of the peptide reagent the immunochemical reaction that takes place is a sandwich reaction, an agglutination reaction, a competition reaction or an inhibition reaction.

The term "peptide" as used herein refers to a molecular chain of amino acids with a biological activity, and does not refer to a specific length of the product. Thus inter alia, proteins, fusion proteins or fusion peptides, oligopeptides and polypeptides are included.

If required peptides which are preferably used in a peptide reagent according to the invention can be modified in vivo or in vitro, for example by glycosylation, amidation, carboxylation or phosphorylation. Functional variants like, for example, acid addition salts, amides, esters, and specifically C-terminal esters, and N-acyl derivatives of said peptides are therefore also considered part of the present invention. It will be understood that for the particular proteins or polypeptides embraced herein, natural variations can also exist. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous proteins.

The term "at least a part of" as used herein means an amino acid sequence comprising a subsequence of a peptide which is preferably used in a peptide reagent according to the invention. Said part or fragment is a peptide having one or more immunogenic determinants of the CMV pp28 (UL99), pp150 (UL32), pp72(UL122/123), pp65(UL83), pp52(UL44), pp38(UL80), gB(UL55) and MDBP(UL57) proteins. Fragments can inter alia be produced by enzymatic cleavage of precursor molecules, using restriction endonucleases for the DNA and proteases for the polypeptides. Other methods include chemical synthesis of the fragments or the expression of peptide fragments by DNA fragments.

Suitable antigenic or immunogenic fragments of said peptides containing (an) epitope(s) can be found by means of the method described in European Patent EP 0 220 245, Geysen, H. M. et al. (Proc. Natl. Acad. Sci. 81, 3998–4002, 1984), Geysen, J. M. et al., (J. Immunol. Meth. 102, 259–274, 1987) based on the PEPSCAN method, wherein a series of partially overlapping peptides corresponding with partial sequences of the complete polypeptide under consideration, are synthesized and their reactivity with antibodies is investigated.

In addition, a number of regions of the peptides can be designated epitopes on the basis of theoretical considerations, although the predictive value of these theoretical considerations is limited. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

The preparation of the peptides or fragments thereof that are preferably used in a peptide reagent according to the invention is effected by means of one of the known organic chemical methods for peptide synthesis or with the aid of recombinant DNA techniques.

The organic chemical methods for peptide synthesis are considered to include the coupling of the required amino acids by means of a condensation reaction, either in homogenous phase or with the aid of a solid phase.

The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of above-mentioned peptides using the "solid phase method" is for instance described in J. Amer. Chem. Soc. 85, 2149 (1963) and Int. J. Peptide Protein Res. 35, 161–214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine-function.

A particularly suitable solid phase is, for example, the p-alkoxybenzyl alcohol resin (4-hydroxy-methyl-phenoxy-methyl-copolystrene-1% divinyl-benzene resin), described by Wang (1974; J. Am. Chem. Soc. 95, 1328). After synthesis the peptides can be split from this solid phase under mild conditions.

After synthesis of the desired amino acid sequence, detaching of the peptide from the resin follows, for example, with trifluoromethane-sulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzene-sulphonyl or p-toluenesulphonyl group, but other groups can also be used, such as substituted or unsubstituted aryl or aralkyl groups, for example benzyl and triphenylmethyl, or groups such as orthonitrophenyl-sulphenyl and 2-benzoyl-1-methyl-vinyl. A particularly suitable Â-amino-protective group is, for example, the base-sensitive 9-fluorenyl-methoxycarbonyl (Fmoc) group [Carpino & Han (1970) J. Amer. Chem. Soc. 92, 5748].

A more extensive account of possible protecting groups can be found in The Peptides, Analysis, Synthesis, Biology, Vol. 1–9 (Eds. Gross, Udenfriend and Meienhofer) 1979–1987 (Academic Press, Inc.).

It is necessary also to protect the ε-amino group of lysine and advisable for the guanidine group of arginine. Customary protective groups in this connection are a Boc-group for lysine and a Pmc- or Pms- or Mbs-group or Mtr-group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

The immunoreactive peptides that are used in a peptide reagent according to the present invention can also be combined in a single molecule. The covalent linkage of two or more peptides in a hybrid- or combi-peptide can for instance be carried out through solid phase peptide synthesis, using the methods described above, of a peptide sequence wherein the amino acid sequences of the individual peptides are aligned. It is understood that a linker sequence may be inserted between the individual peptides sequences. Such a linker sequence may for instance be a stretch of 2–5 residues of glycine.

A hybrid- or combi-peptide can also be prepared through solid phase synthesis using the fragment condensation approach. The latter method, in which the fragments (the sequences of which may correspond with the sequences of the individual peptides of the invention) are separately prepared and purified, is preferred in the synthesis of the longer hybrid- or combi-peptide sequences. The methodology for the preparation of longer peptides is known in the art, and for instance described in The Peptides, Analysis, Biology, Vol. 1–9 (vide supra).

Alternatively, hybrid- or combi-peptides can be prepared through conjugation of appropriately modified peptides of the present invention.

In a preferred method for the conjugation of two different peptide sequences which are devoid of the amino acid cysteine, the peptides are derivatized to contain an additional residue of cysteine at either the carboxyl- or the amino-terminal end. One of the peptides is subsequently activated at the single cysteine thiol function with 2,2'-dithiodipyridine. The resulting pyridyl-dithio-peptide derivative is then reacted with the second peptide containing the cysteine thiol group to yield a hybrid peptide in which the individual peptides are linked through a disulfide bond.

Numerous other methods for the preparation of hybrid peptides can be envisaged. Use can be made of the chemical methodology that has been developed in the field of protein-protein conjugation. An overview of such methods is given by Means and Feeney (Bioconj. Chem. 1, 2–12, 1990). For instance, the use of well known homo- or heterobifunctional cross-linking agents allow the coupling of individual peptides through a disulfide bond, or a thioether or amide bond, or the like.

As already indicated above, the peptides that are preferably used in a peptide reagent according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide or as a fusion protein with, for example, (part of) β-galactosidase. This type of peptides therefore likewise falls within the scope of the invention. For this purpose, as a constituent of a recombinant DNA, a nucleic acid sequence is used which codes for a peptide according to the invention and which, furthermore, is substantially free from nucleic acid segments, which in the naturally occurring CMV genome flank the nucleic acid sequence indicated above.

This latter method involves the preparation of the desired peptide by means of bringing to expression a recombinant polynucleotide with a nucleic acid sequence which is coding for one or more of the peptides in question in a suitable micro-organism as host.

A nucleic acid sequence encoding a peptide as used in a peptide reagent according to the present invention can be ligated to various replication effecting DNA sequences with which it is not associated or linked in nature resulting in a recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences are known in the art and include inter alia plasmid vectors such as pBR322, the various pUC, pGEM and Bluescript plasmids, bacteriophages, e.g. kgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule are known to those of ordinarily skill in the art and are inter alia set forth in Maniatis, T. et al. (Molecular Cloning A Laboratory Manual, second edition; Cold Spring Harbor Laboratory, 1989).

For example, the insertion of the nucleic acid sequence encoding a peptide according to the invention into a cloning vector can easily be achieved when both the genes and the desired cloning vehicle have been cut with the same restriction enzyme(s) as complementary DNA termini are thereby produced.

The recombinant vector molecules may additionally contain one or more marker activities that may be used to select for desired transformants, such as ampicillin and tetracycline resistance in pBR322, as for example ampicillin resistance and α-peptide of β-galactosidase in pUC8.

It should, of course, be understood that the nucleotide sequences inserted at the selected site of the cloning vector may include only a fragment of the complete nucleic acid sequence encoding for peptides used in a peptide reagent according to the invention as long as the transformed host will produce a polypeptide having at least one or more antigenic or immunogenic determinants.

Antibodies, directed to said peptides are also part of the present invention.

The peptides or fragments thereof prepared and described above can be used to produce antibodies, both polyclonal and monoclonal.

The monoclonal antibodies according to the present invention, therefore, provide a new means for the diagnosis of CMV infection.

Preferred antibodies according to the invention are monoclonal antibodies which bind to an epitope of a peptide having the amino acid sequence as shown in SEQ ID No.: 1–10.

More preferred antibodies according to the invention are monoclonal antibodies which bind to an epitope of the CMV pp150 protein, which epitope is recognized by monoclonal antibody CMV.OT3C produced by the hybridoma cell lines deposited with the European Collection of Animal Cell Cultures (ECACC), CAMR (Centre for Applied Microbiology & Research), Salisbury (UK), under deposit No. 96071123.

Immortalized cell lines capable of excreting human or animal (e.g. mouse, rat or chimpanzee) monoclonal antibodies according to the invention are also part of the present invention.

The preparation of cell lines producing monoclonal antibodies may occur by, for example, by the Kohler and Milstein technique (Kohler and Milstein devised the techniques that resulted in the formation monoclonal antibody-producing hybridomas (G. Kohler and C. Milstein, 1975, Nature 256:495–497; 1976, Eur. J. Immunol. 6:511–519)), transformation with Epstein-Barr Virus, or a direct transformation technique of B-lymphocytes with oncogenic DNA, or a direct fusion of human B-lymphocytes with a fusion partner being either a human or a mouse-human hybrid myeloma cell line, or a direct fusion of an EBV-transformed B cell line with said myeloma cell lines.

Preferred cell lines according to the invention are the cell lines deposited at the European Collection of Animal Cell Cultures, CAMR (Centre for Applied Microbiology & Research), Salisbury (UK) under deposit No. 96071123.

These hybridoma cell lines were produced by the fusion of a myeloma cell with a lymphocyte derived from a mouse previously inoculated with CMV-related synthetic peptide molecules (if necessary coupled to keyhole limpet hemacyanin (KLH) in order to enhance their immunogenecity).

Monoclonal antibodies to proteins derived from CMV are useful tools for the detection of CMV expression in cells and cell extracts both in vivo and in vitro, for purification purposes and for a variety of biochemical and immunological analysis techniques to study the function of these proteins.

The term "immunochemically reagent" according to the invention usually consists of one or more (monoclonal) antibodies and a suitable support or a labeling substance.

Supports which can be used are, for example, the inner wall of a microtest well or a cuvette, a tube or capillary, a membrane, filter, test strip or the surface of a particle such as, for example, a latex particle, an aldehyde particle (such as a ceramic magnetizable particle with active aldehyde surface groups), an erythrocyte, a dye sol, a metal sol or metal compound as sol particle, a carrier protein such as BSA or KLH.

Labeling substances which can be used are, inter alia, a radioactive isotope, a fluorescent compound, an enzyme, a dye sol, metal sol or metal compound as sol particle.

The invention further comprises the use of antibodies to said peptide in immunological and biochemical methods aiming to detect the full length protein in a test fluid or tissue specimen.

Antibodies, both monoclonal and polyclonal, directed against peptides according to the invention are very suitable in diagnosis and immunocytochemistry for detection in situ in tissue specimen, while those antibodies which are neutralizing are very useful in passive immunotherapy.

Part of the invention is also the "humanizing" of the monoclonal antibodies in question. Techniques for raising the "humanized" monoclonal antibodies are known in the art.

For the detection of CMV in a sample a peptide reagent according to the invention, containing one or more peptides, can be brought into contact with the sample and anti-CMV after which the presence of immune complexes formed can be detected and, from this, the presence of CMV in a sample can be determined.

A particularly suitable method for the detection of CMV in a sample is based on a competition reaction between a peptide used in said peptide reagent provided with a labeling substance and a CMV antigen (present in the sample) whereby the peptide and the antigen are competing with the antibody directed against CMV attached to a solid support.

The invention further comprises a method for the detection of cytomegalovirus (CMV) in a sample characterized in that an antibody according to the invention is brought into contact with a sample after which the presence of immune complexes formed is detected which is a measure for the presence of CMV in the sample.

A test kit according to the invention comprises as an essential constituent a peptide reagent as described above. Carrying out a sandwich reaction, for the detection of CMV antibodies the test kit may comprise, for example, a peptide used in a peptide reagent according to the invention coated to a solid support, for example the inner wall of a microtest well, and either a labeled peptide used in a peptide reagent according to the invention or a labeled anti-antibody.

For carrying out a competition reaction, the test kit may comprise a peptide used in a peptide reagent according to the invention coated to a solid support, and a labeled antibody directed against CMV preferably a monoclonal antibody directed against said peptide.

In an agglutination reaction the test kit comprises a peptide reagent comprising a peptide coated to particles or sols.

Another embodiment of a test kit is, for example, the use of a labeled peptide used in a peptide reagent according to the present invention in a competition reaction with a CMV antigen to be detected for a binding site on the antibody directed against CMV, which is coated to a solid support.

The above disclosure generally describes the present invention. A more complete understanding can be obtained by reference to the following specific examples which are provided for purposes of illustration only, and are not intended to limit the scope of the invention.

BRIEF DESCRIPTION OF THE FIGURES

Peptide Code Definition:
K-38-E (pp150): SEQ.ID.No. 1
T-21-C (pp150): SEQ.ID.No.2
C-21-M (pp150): SEQ.ID.No.3
T21CC21M (pp150): SEQ.ID.No.4
OTP194(pp150): SEQ.ID.No.5
OTP197(pp150): SEQ.ID.No.6
OTP101A (gB): SEQ.ID.No.7
F-28-G (pp52): SEQ.ID.No.8
OTP118A(pp28): SEQ.ID.No.9
OTP119A (pp28): SEQ.ID.No.10

A=the relative absorbance values for each individual serum tested

B=the sum of individual absorbance values for each peptide, corrected for the background value for each serum C=the positivity-score for each peptide yielding an absorbence value of at least 3 SD above the mean background value for each serum tested.

FIGS. 2A–2K
Analyses representing the best set of peptides reacting with IgG antibodies using sera from patients with active CMV-infections and appropriate controls without active CMV-infections.

FIGS. 3A–3D
Analyses representing the best set of peptides reacting with IgM antibodies using sera from random healthy individuals seropositive or seronegative for CMV antibodies as determined by reference antibody assays.

FIGS. 4A–4B

Comparison of the reactivity of human IgG with cell culture derived CMV-Ag (horizontal axis) versus a CMV peptide reagent [#K38E+#OTP101A+#OTP119A] (SEQ ID No. 1+SEQ ID No. 7+SEQ ID No. 10).

FIG. 5:

A comparison of the reactivity of human serum IgM is shown with cell culture derived CMV-Ag (horizontal axis) versus a CMV peptide reagent [#K38E+#F28G] (SEQ.ID.No. 1+SEQ.ID.No. 8) on the vertical axis.

FIG. 6:

Immunoblot detection of CMV-pp150(UL32) using CMV.OT3C. Control reactions with monoclonal antibodies to additional CMV proteins (GICR series obtained from Goodwin Institute for Cancer Research, Florida, USA) and human serum IgG from a CMV-seropositive donor are shown in the parallel strips as indicated in the legend below the figure.

The Invention is Further Exemplified by the Following Examples:

EXAMPLE 1

Peptides with a length of 12 amino acids (AA) and overlapping by 11 AA of the AA sequence of the complete UL99 reading frame reading frame encoding CMV-pp28 were synthesized by automated solid phase synthesis onto chemically activated pins as originally described by Geysen et al (P.N.A.S., USA, 83 (1984) p.3998–4002).

The immunoreactivity of each peptide with CMV-specific antibodies from human sera (10 CMV seropositive individuals) was determined as described by Middeldorp and Meloen (J. Virol. Meth. 21 (1988) p.147–159).

Figure 1:
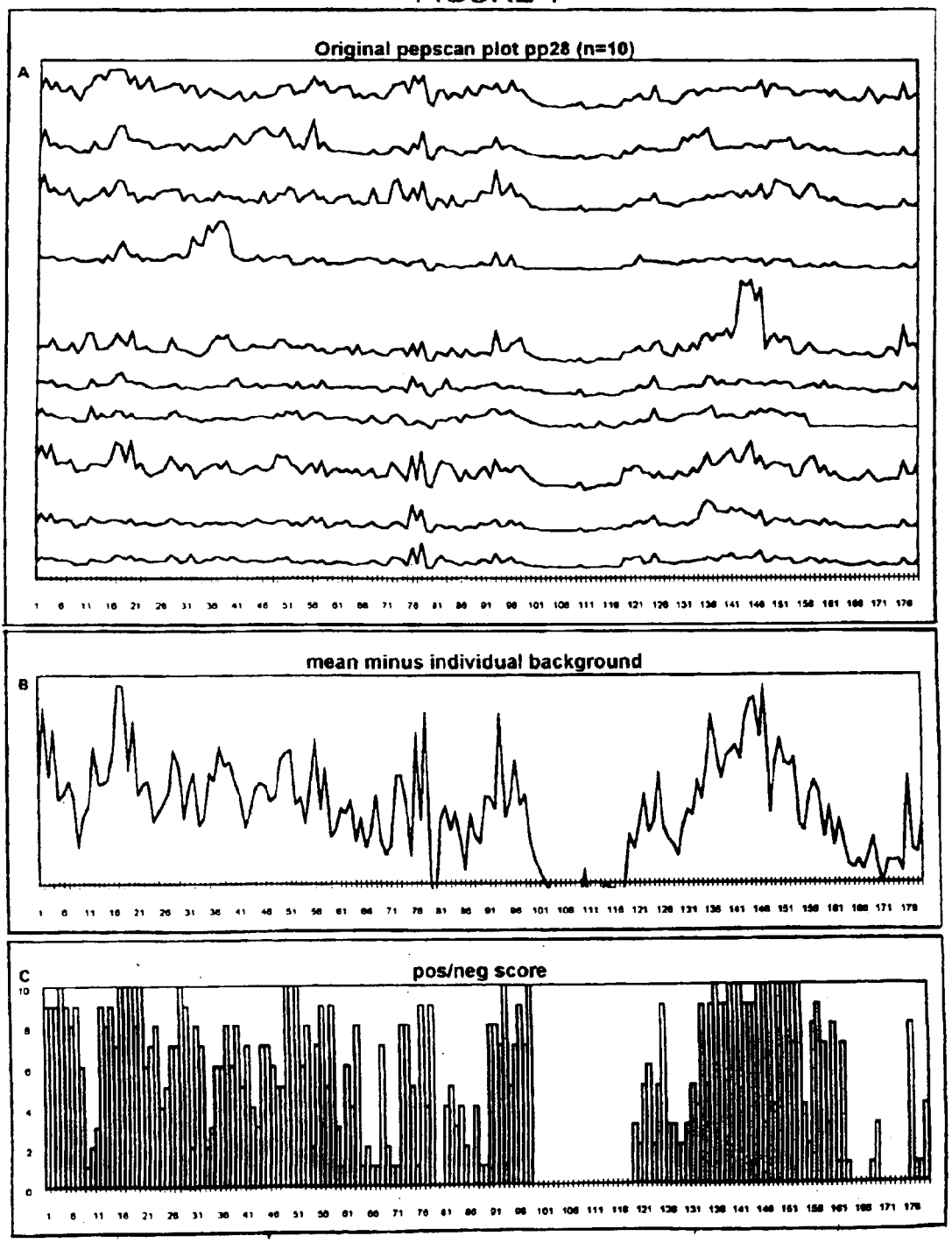
FIG. 1:
Identification of binding sites for human IgG antibodies (10 sera of CMV seropositive individuals) on CMV-pp28 (UL99) by peptide-scanning ELISA.
Figure 2A:
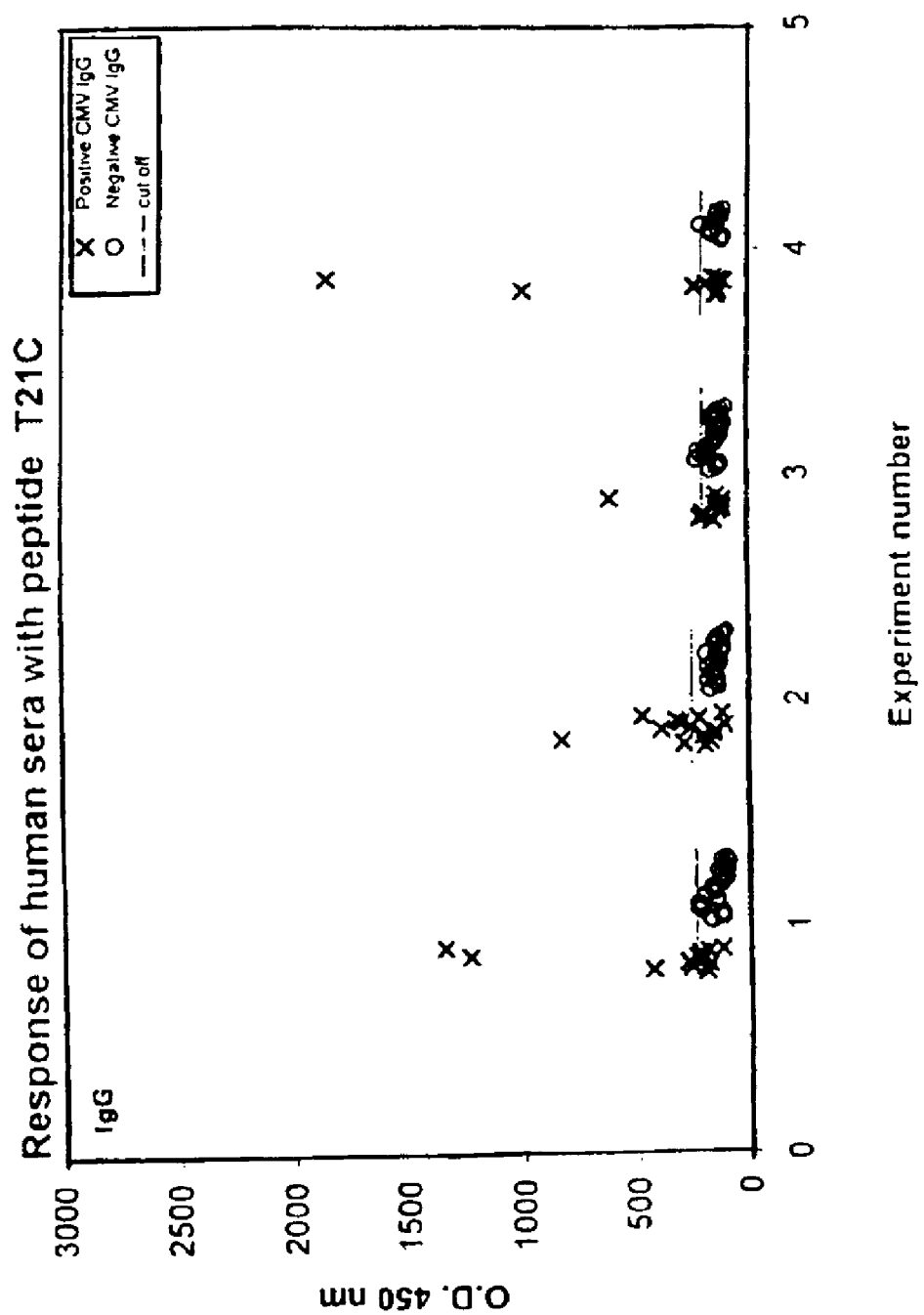
Figure 2B:
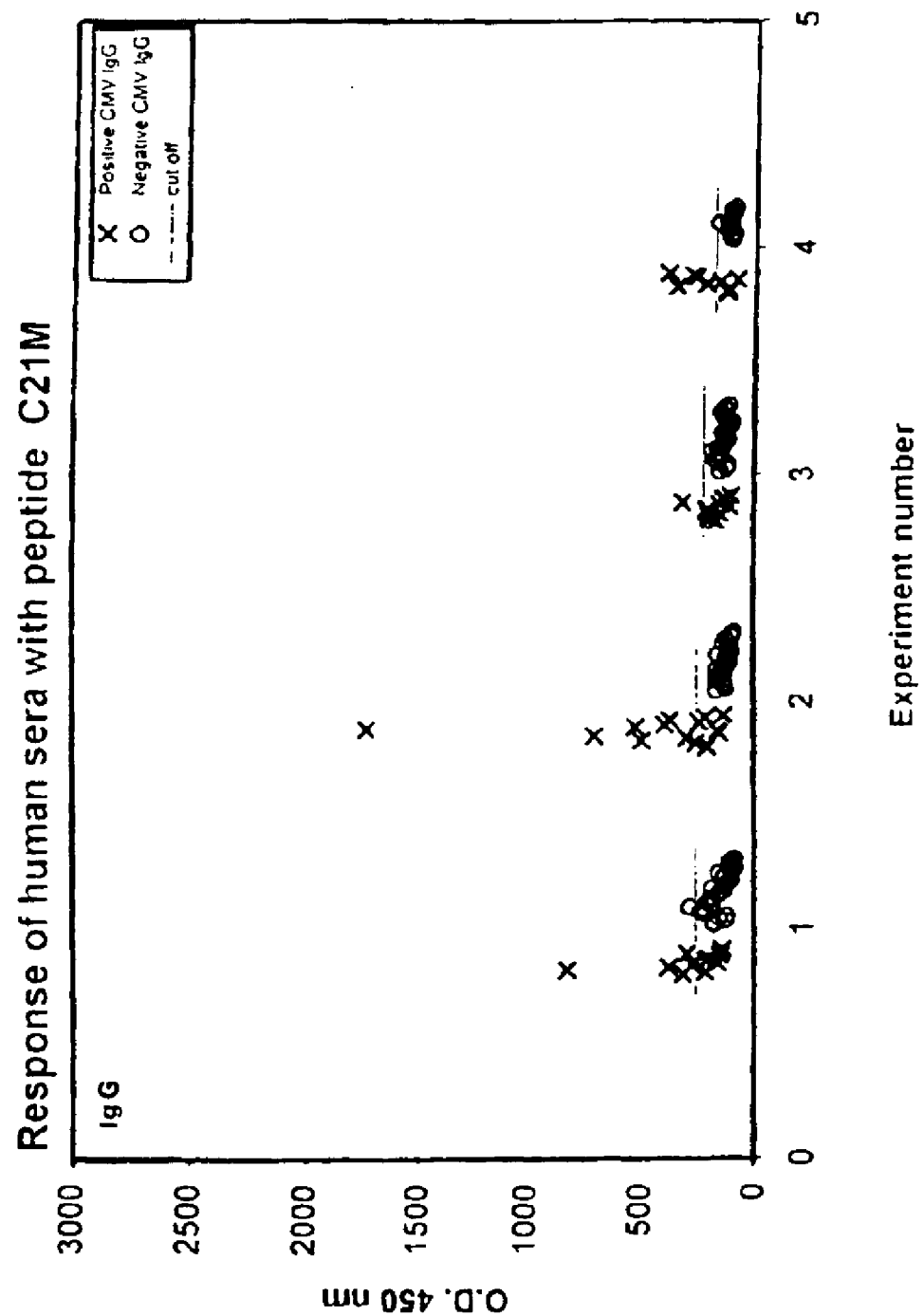
Figure 2C:
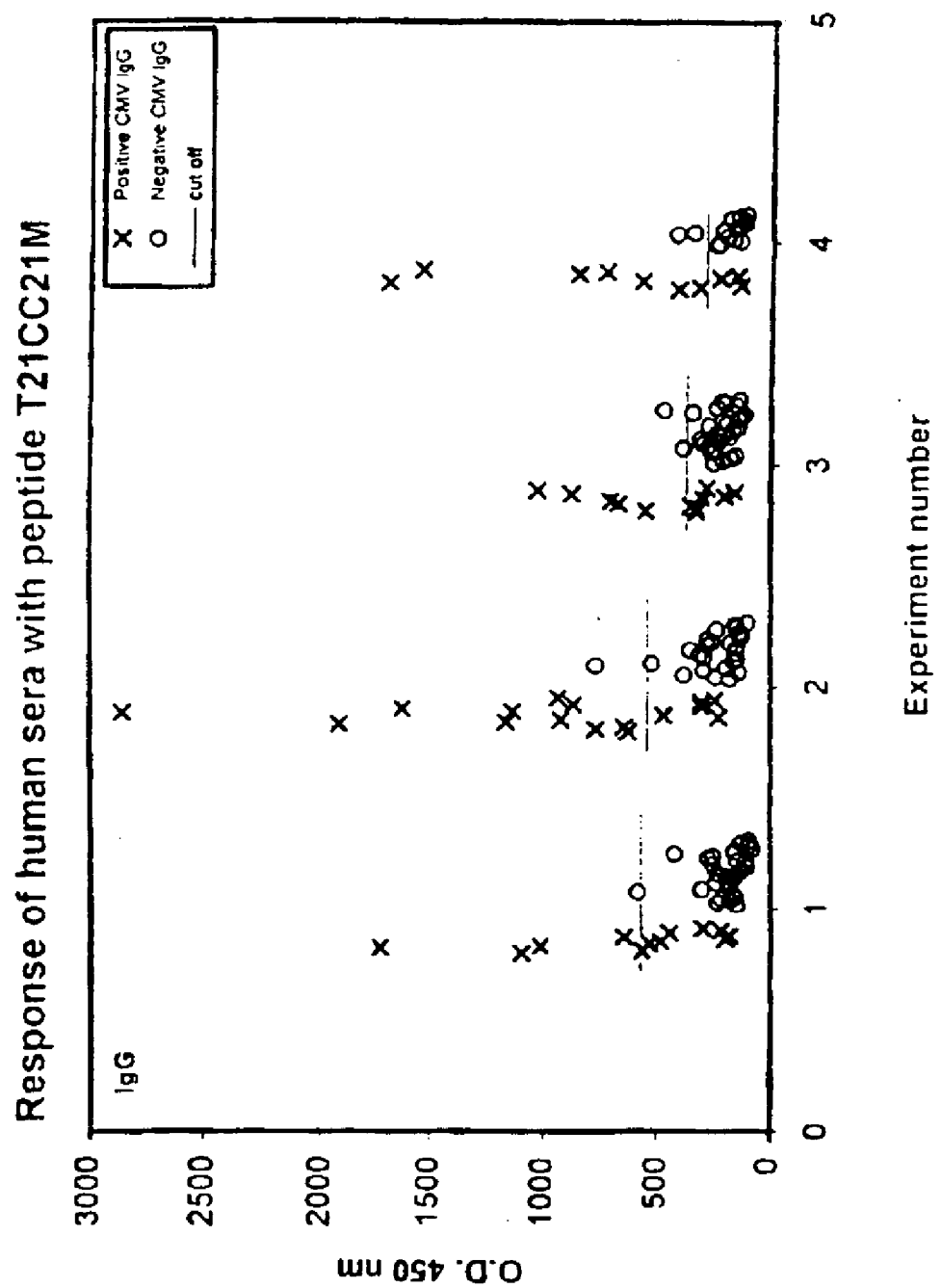
Figure 2D:
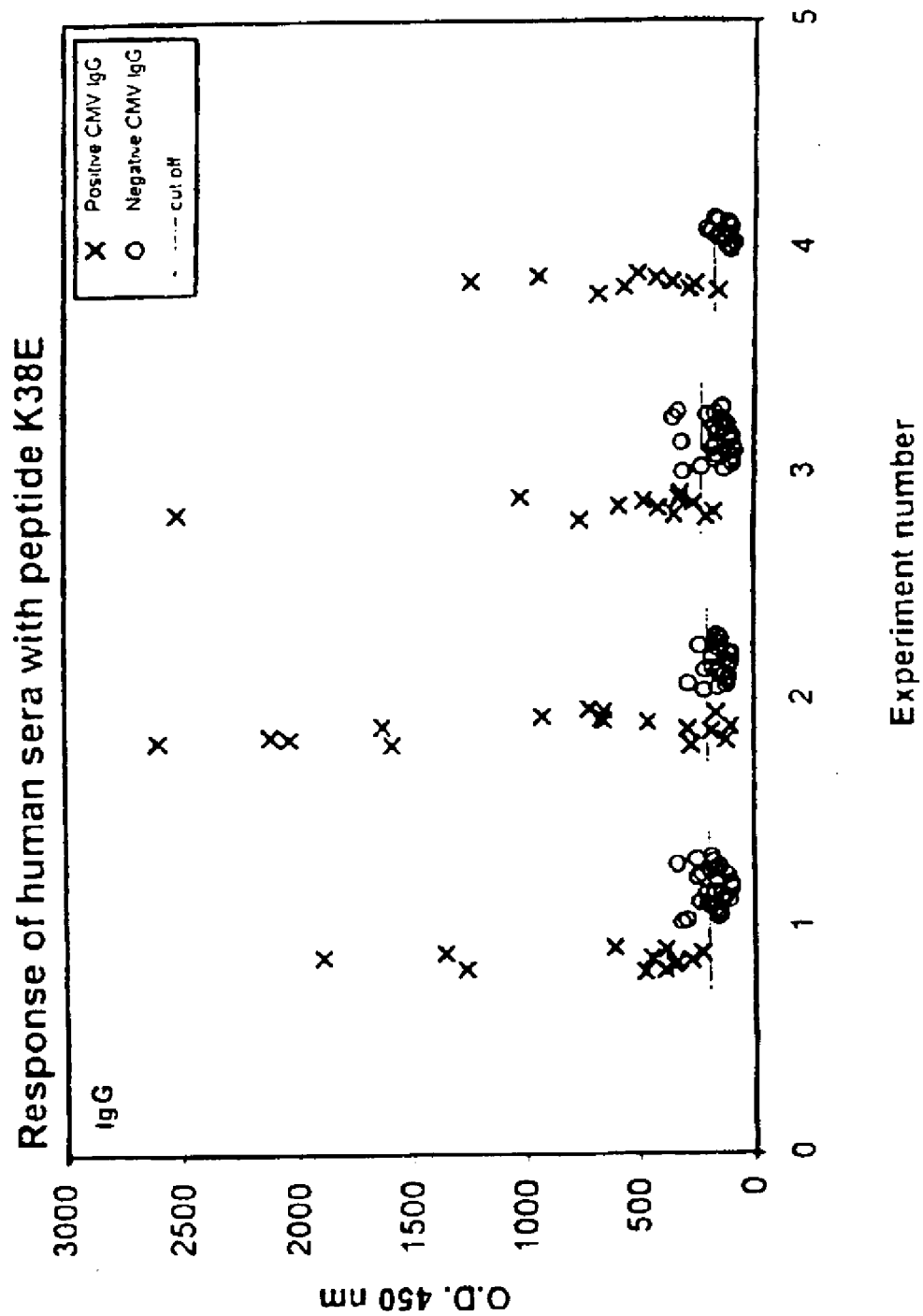
Figure 2E:
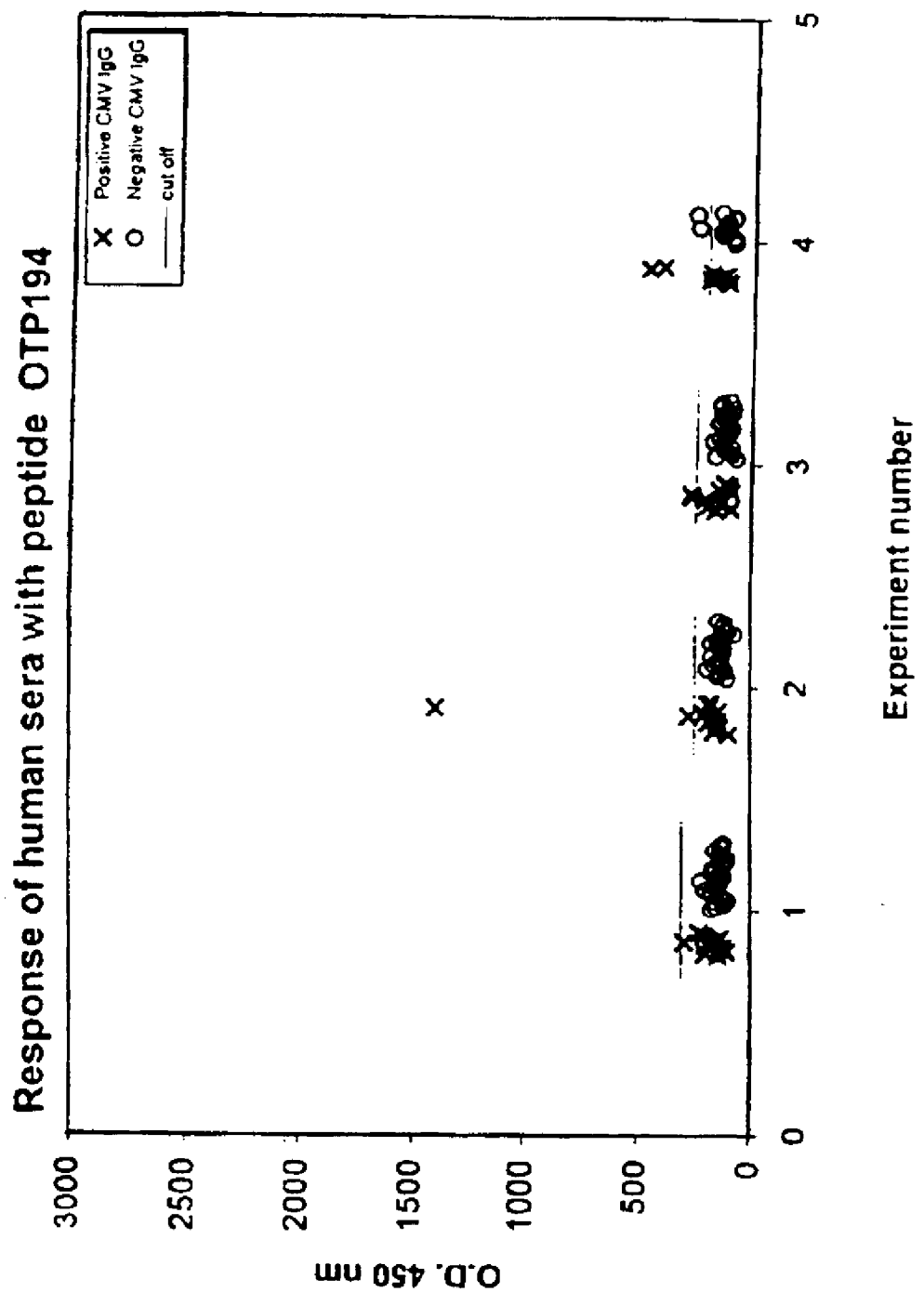
Figure 2F:
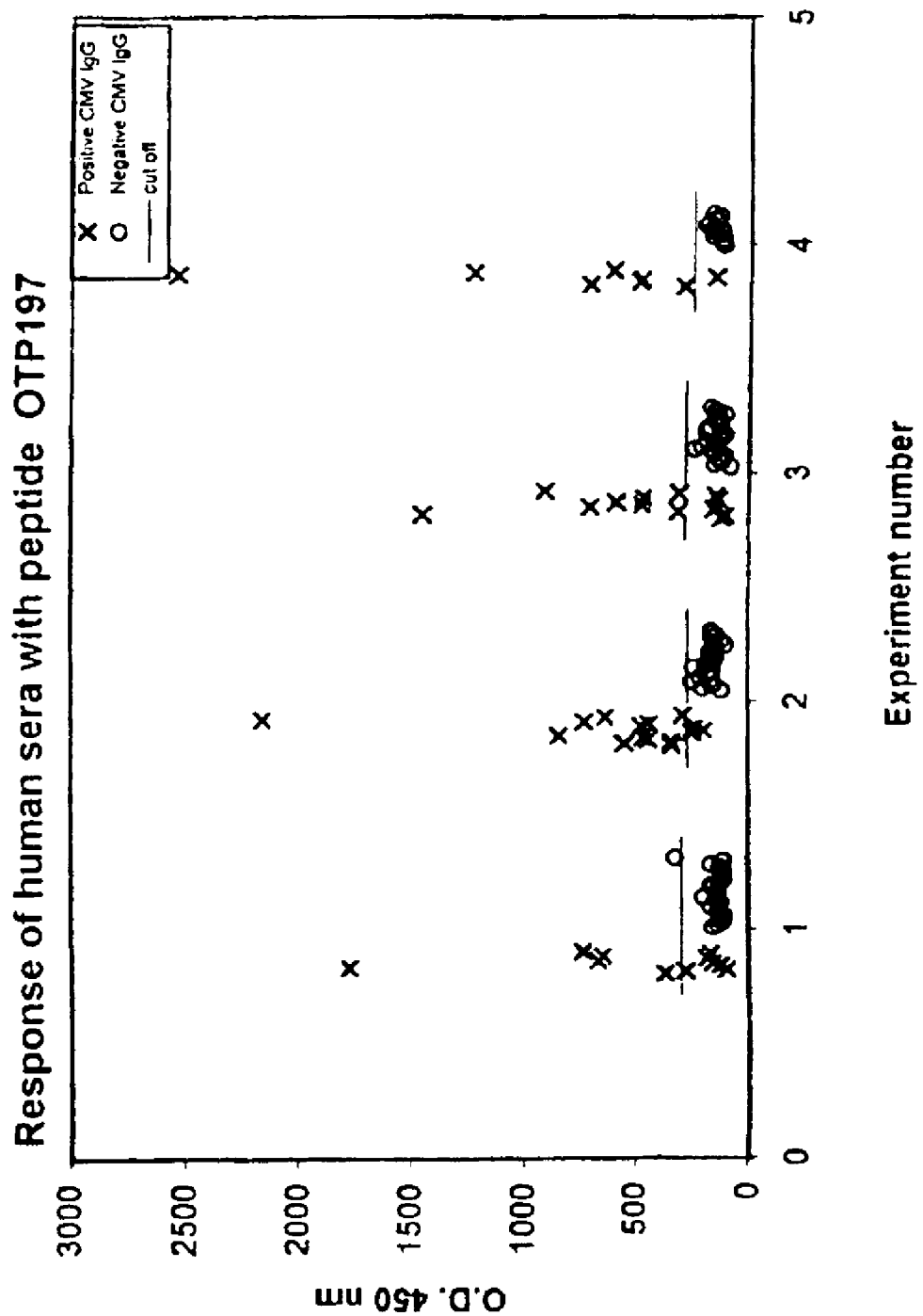
Figure 2G:
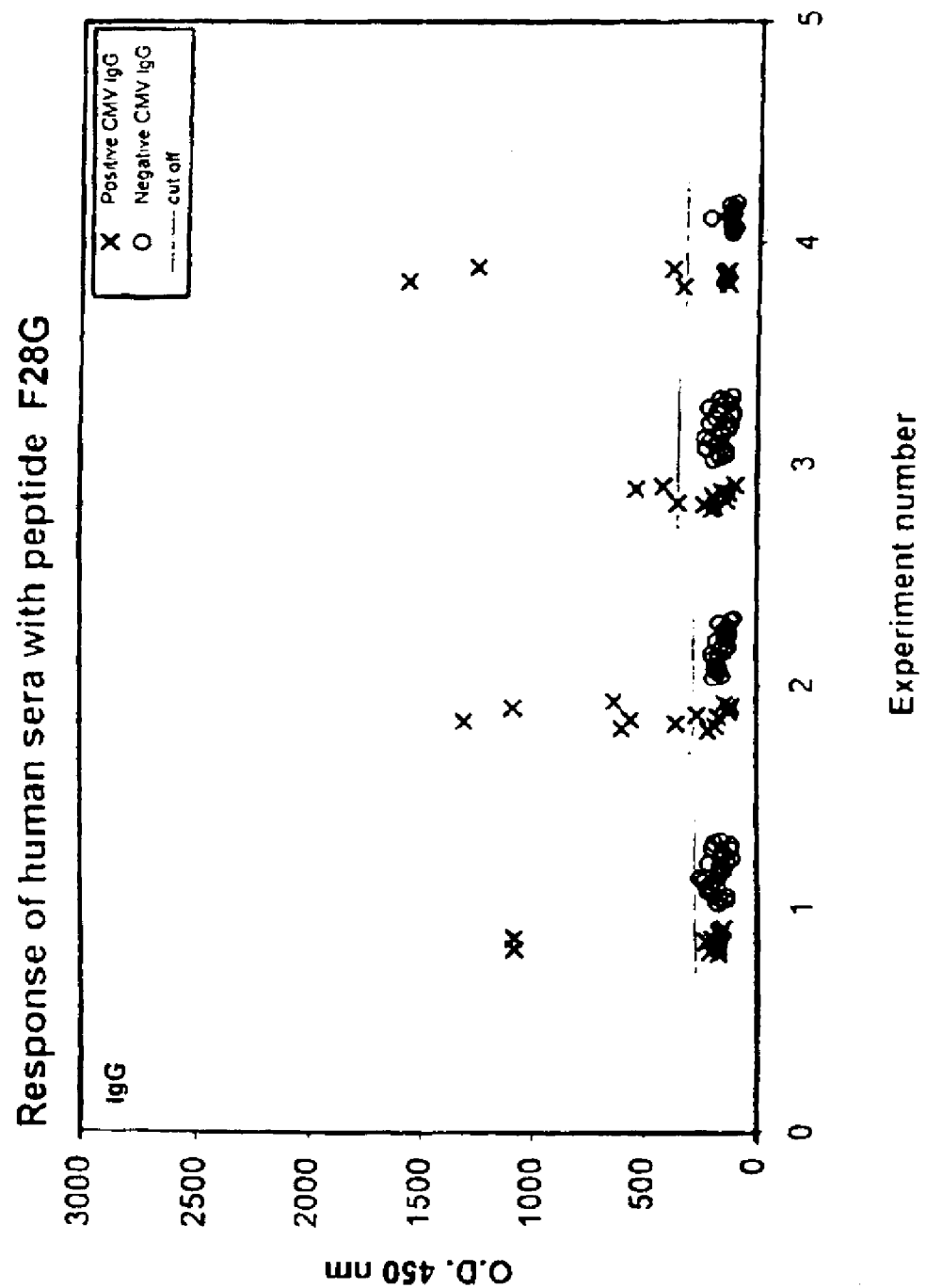
Figure 2H:
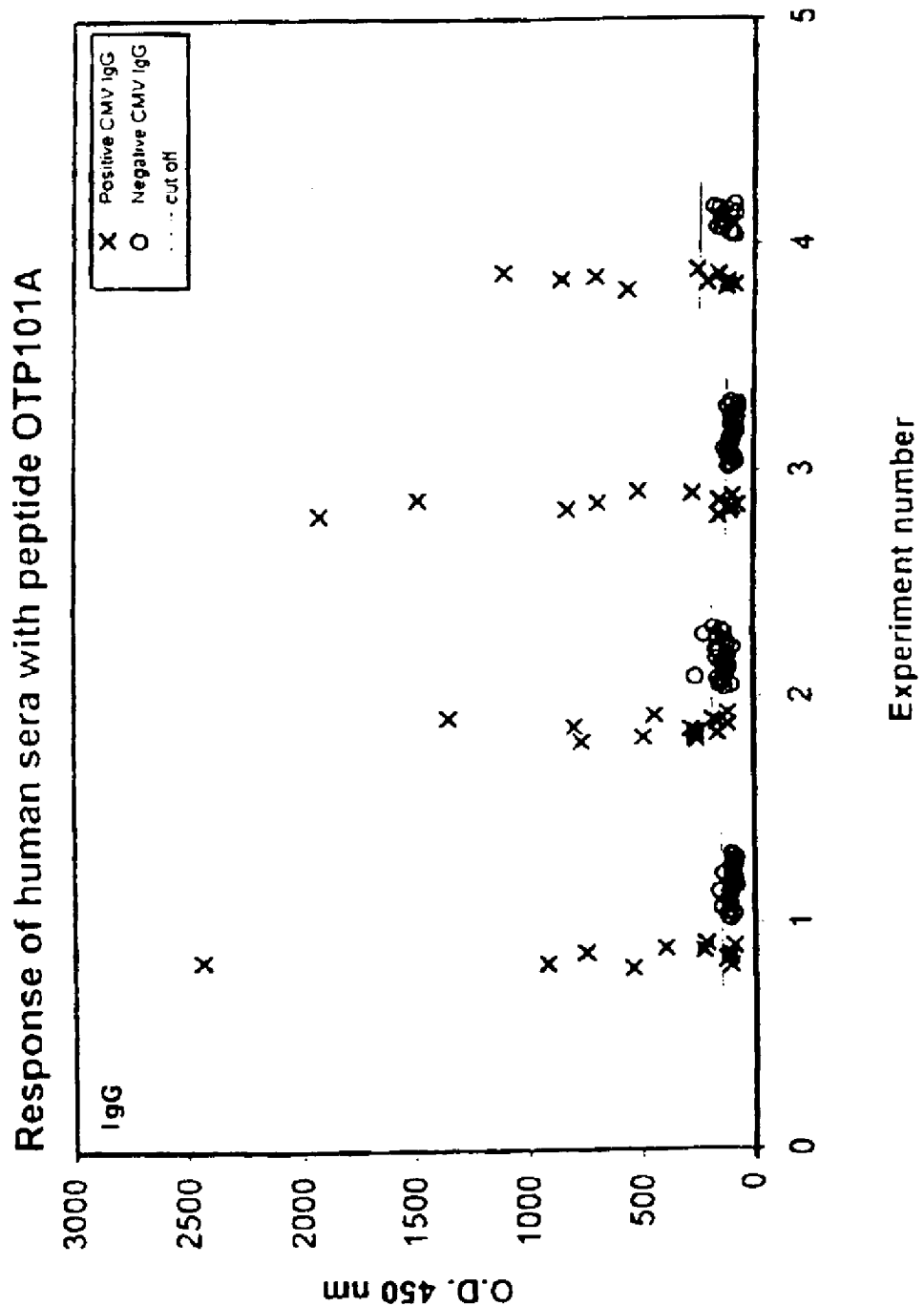
Figure 2I:
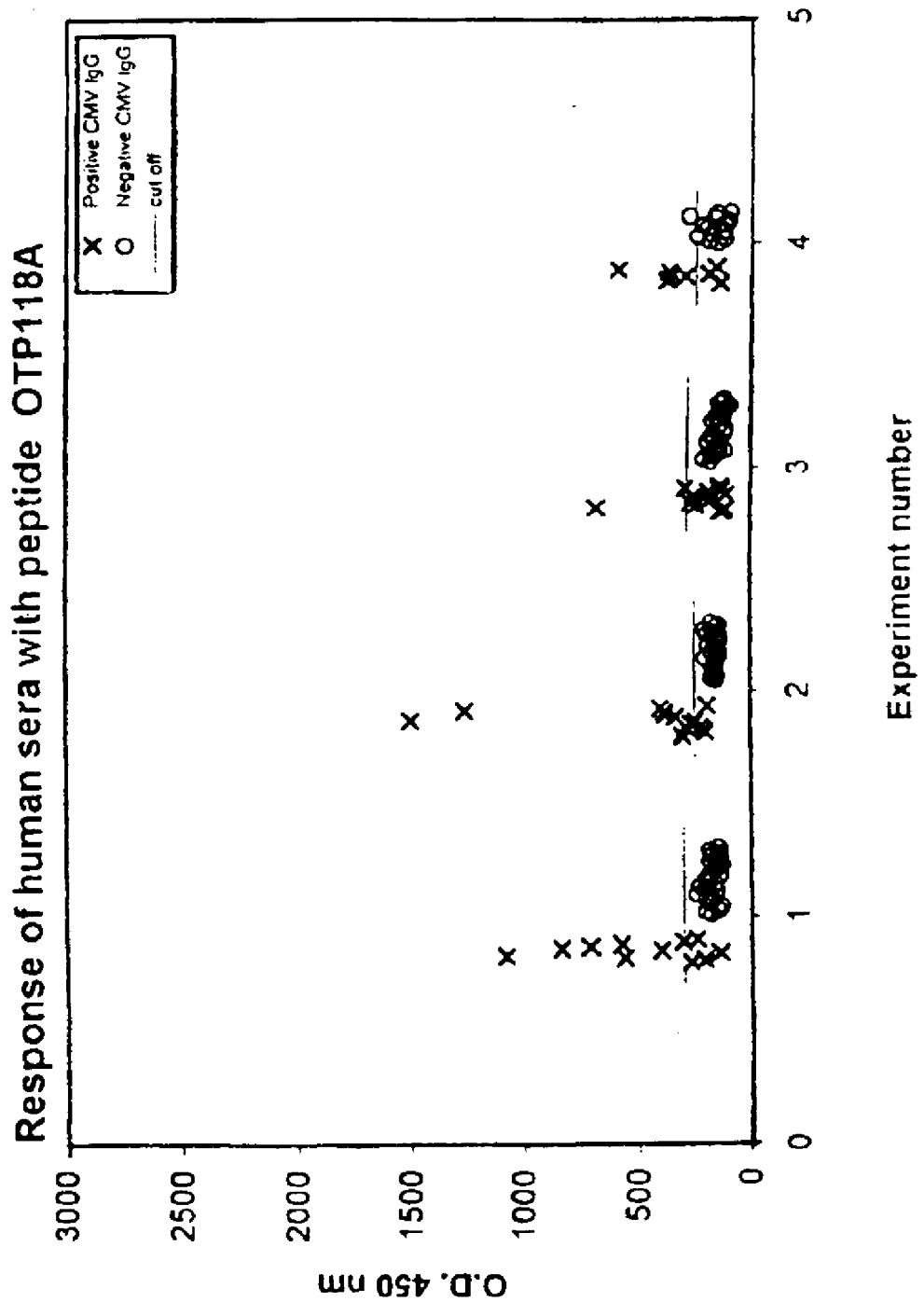
Figure 2J:
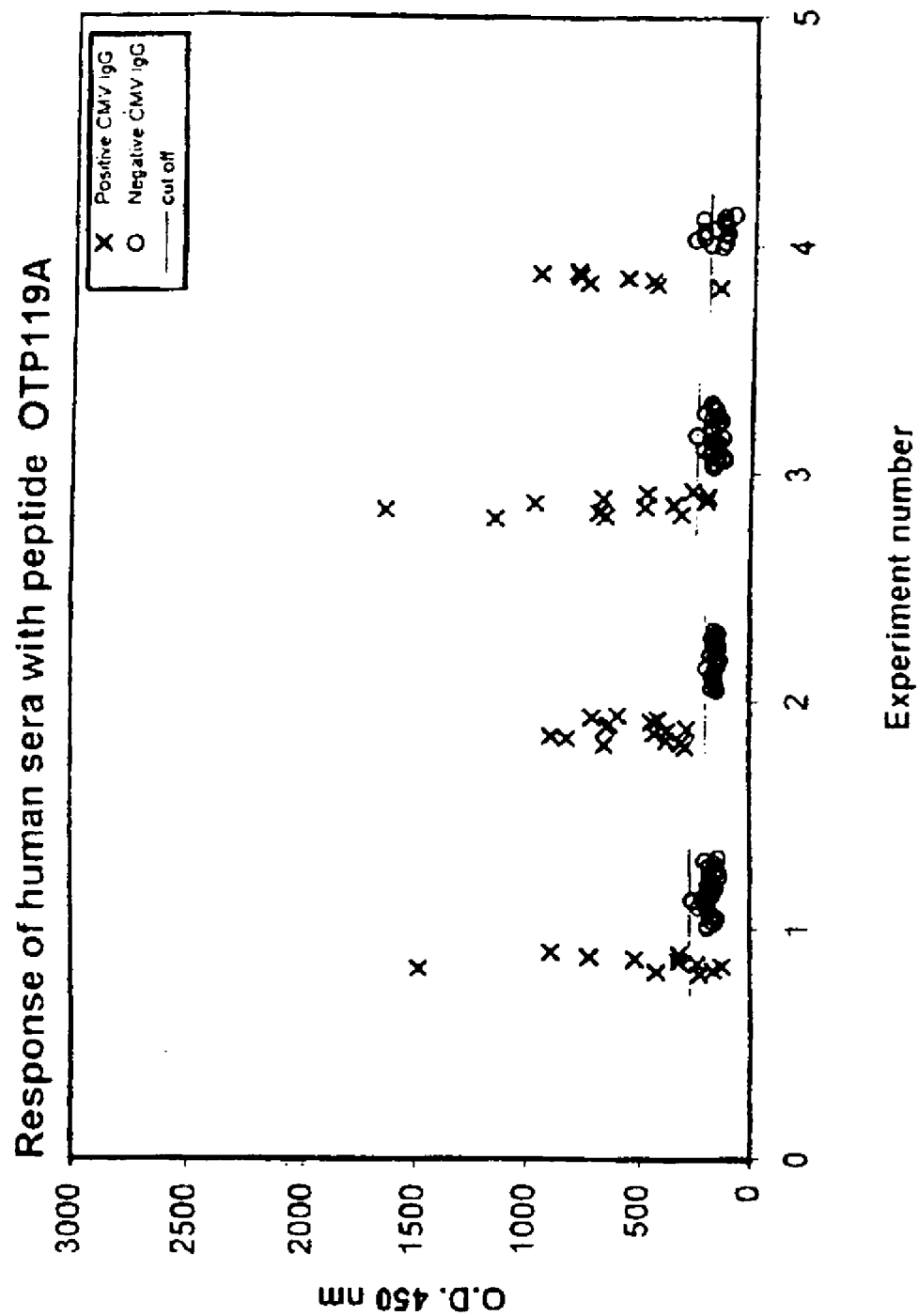
Figure 2K:
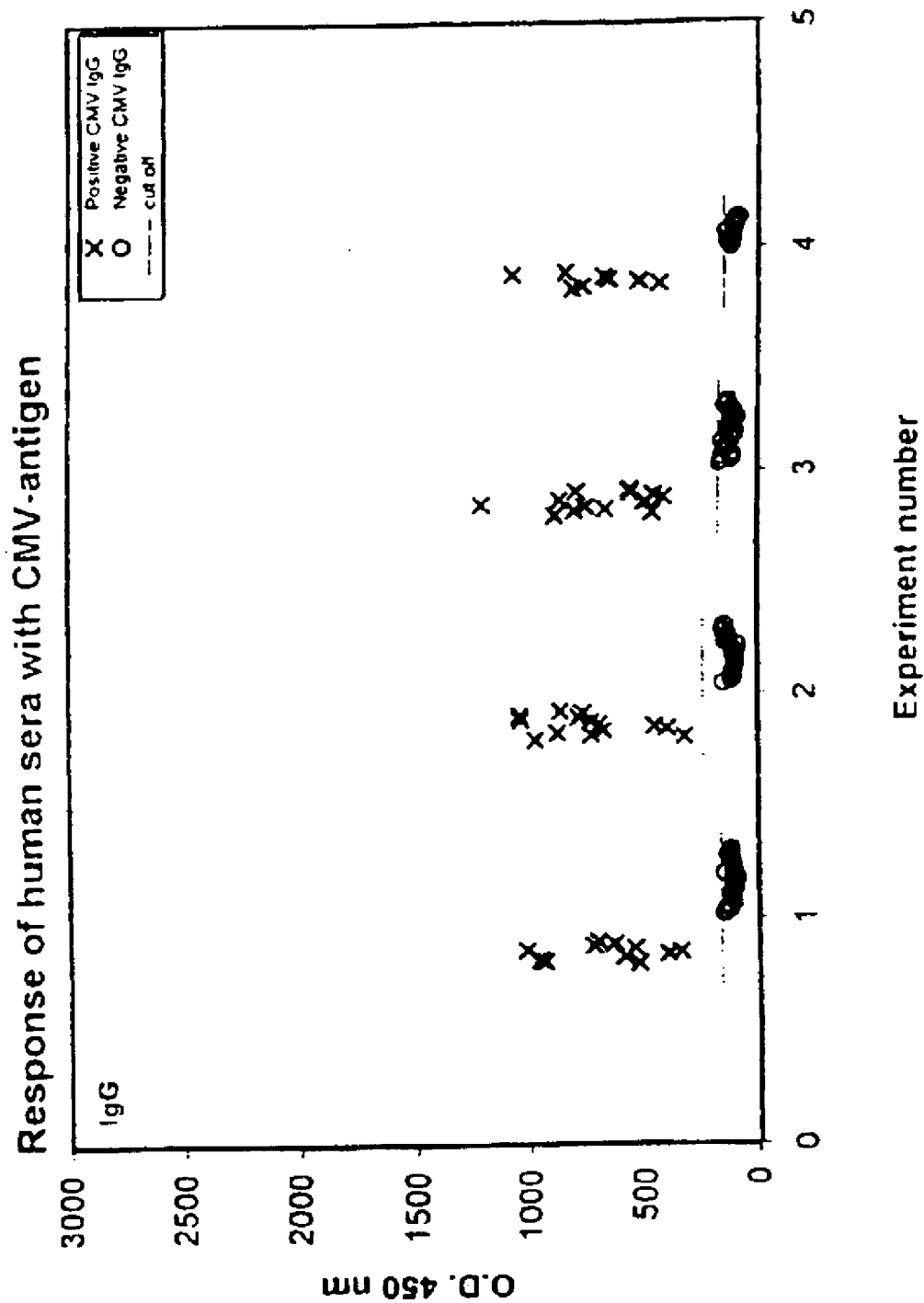
Figure 3A:
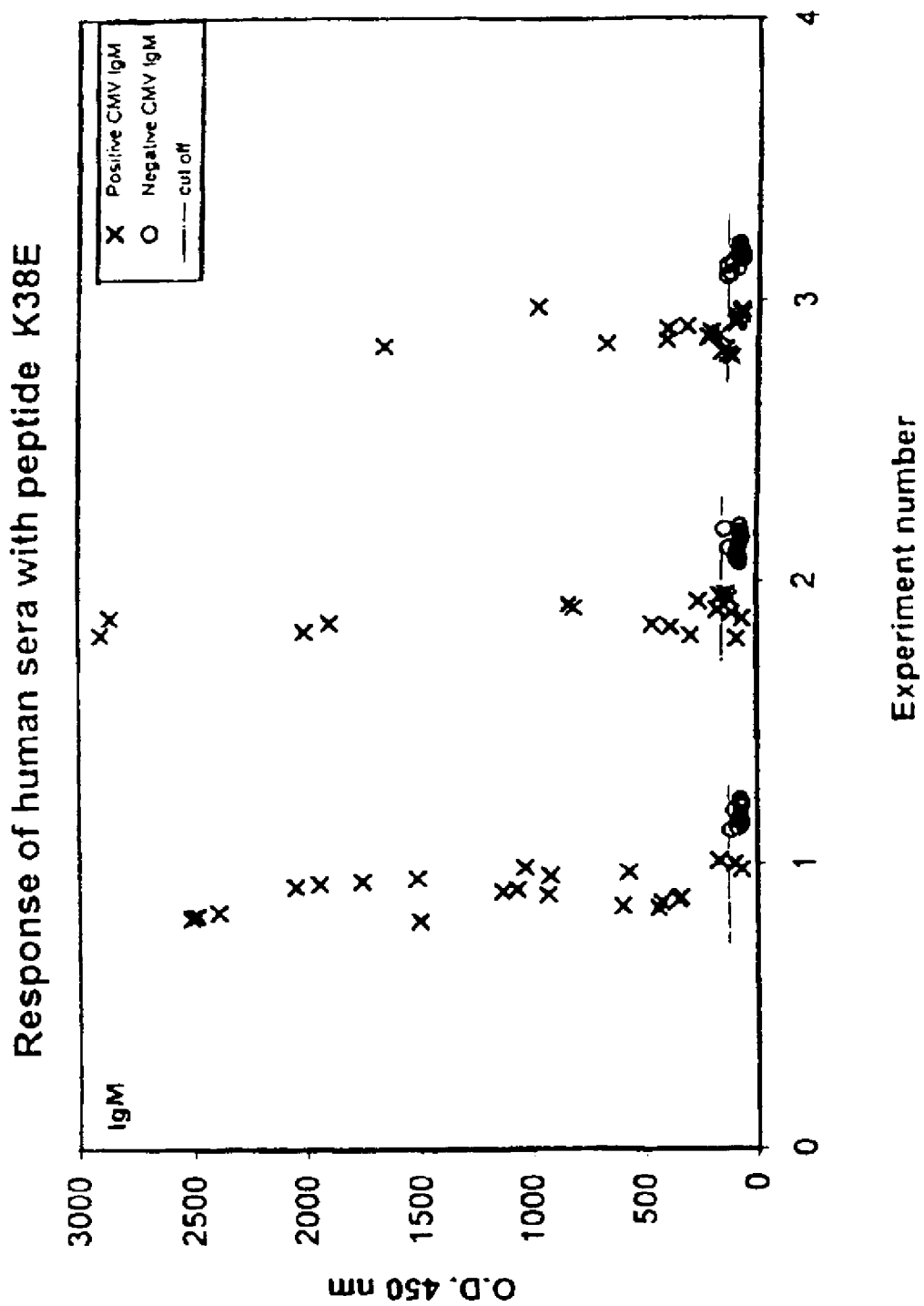
Figure 3B:
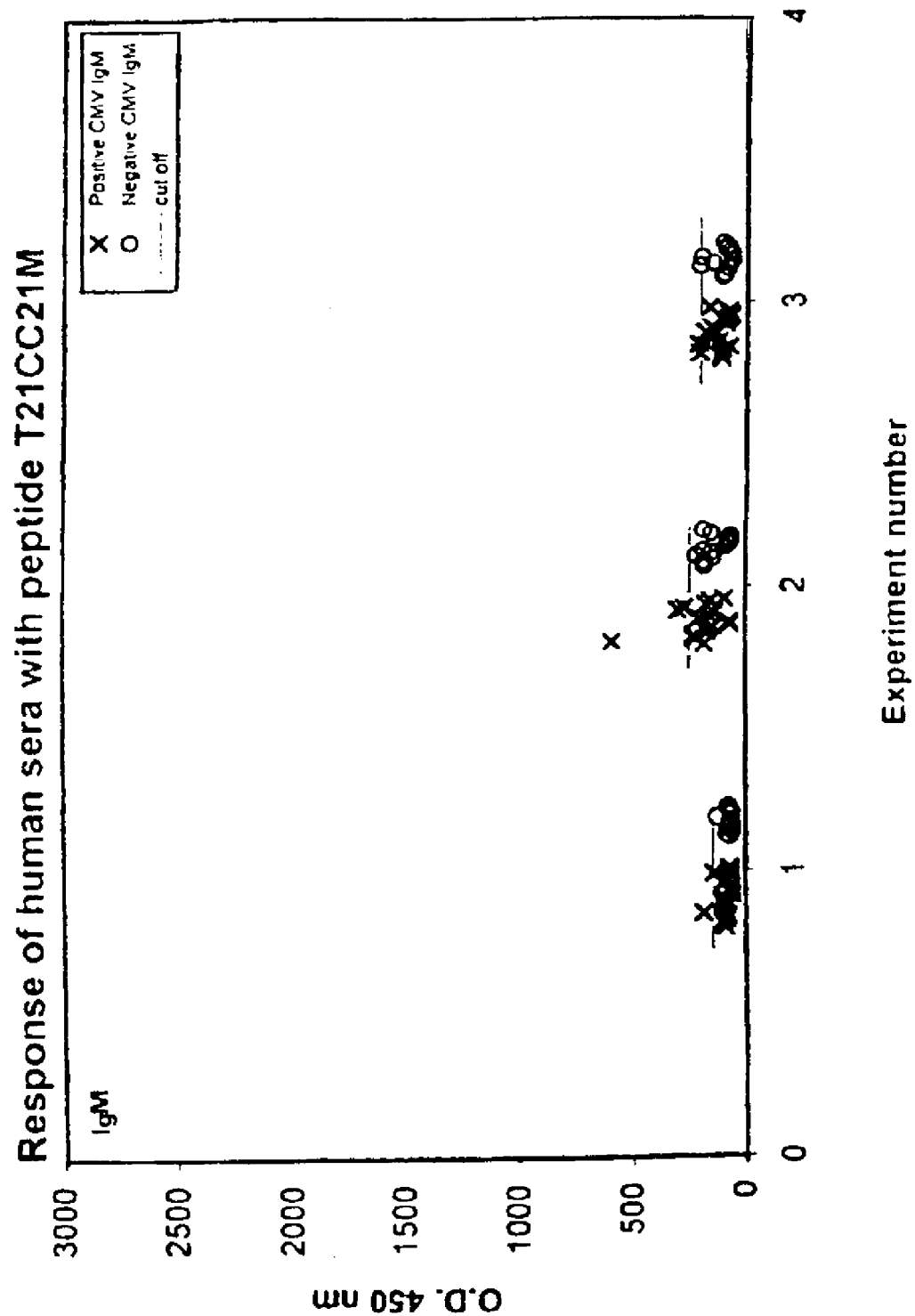
Figure 3C:
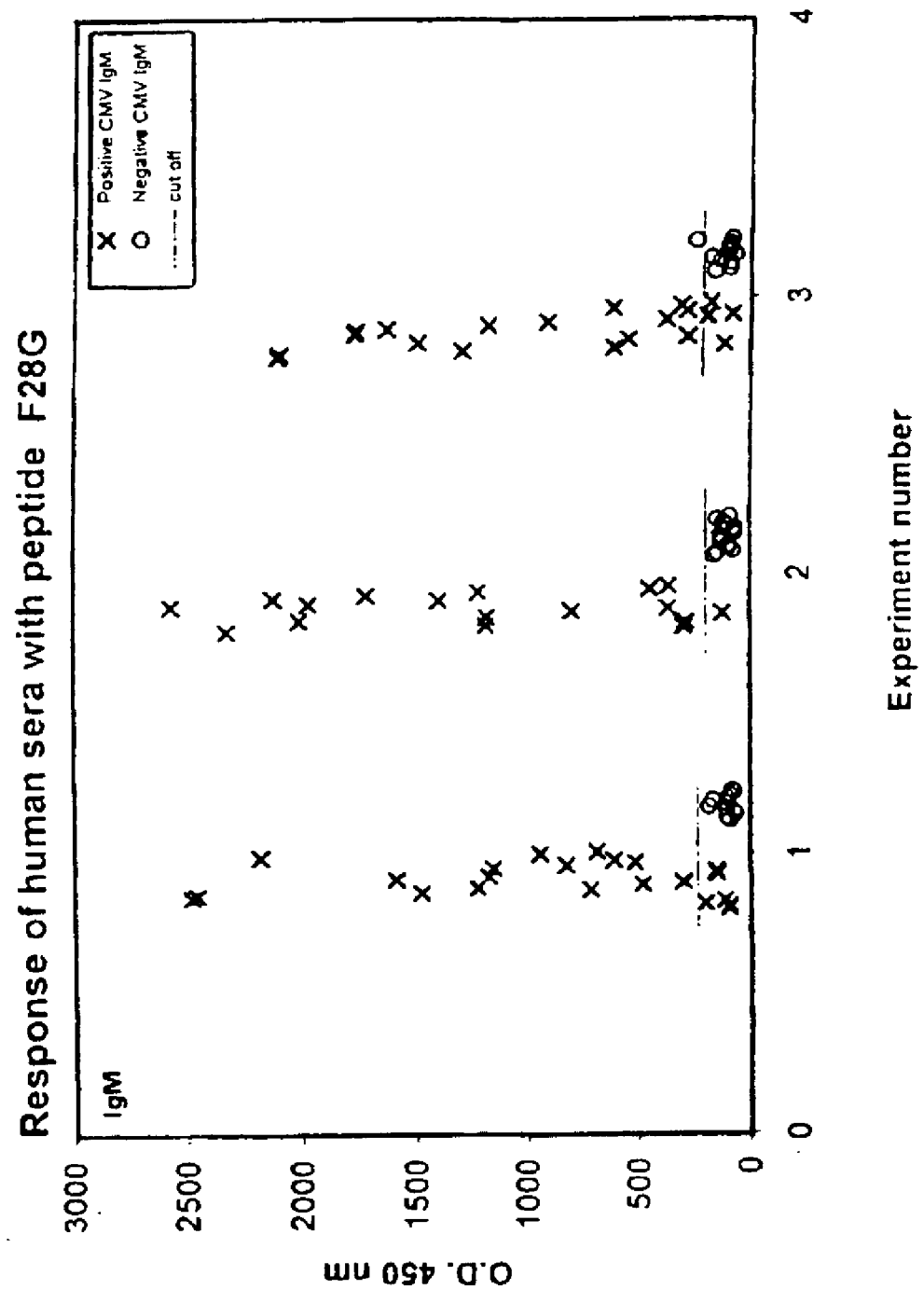
Figure 3D:
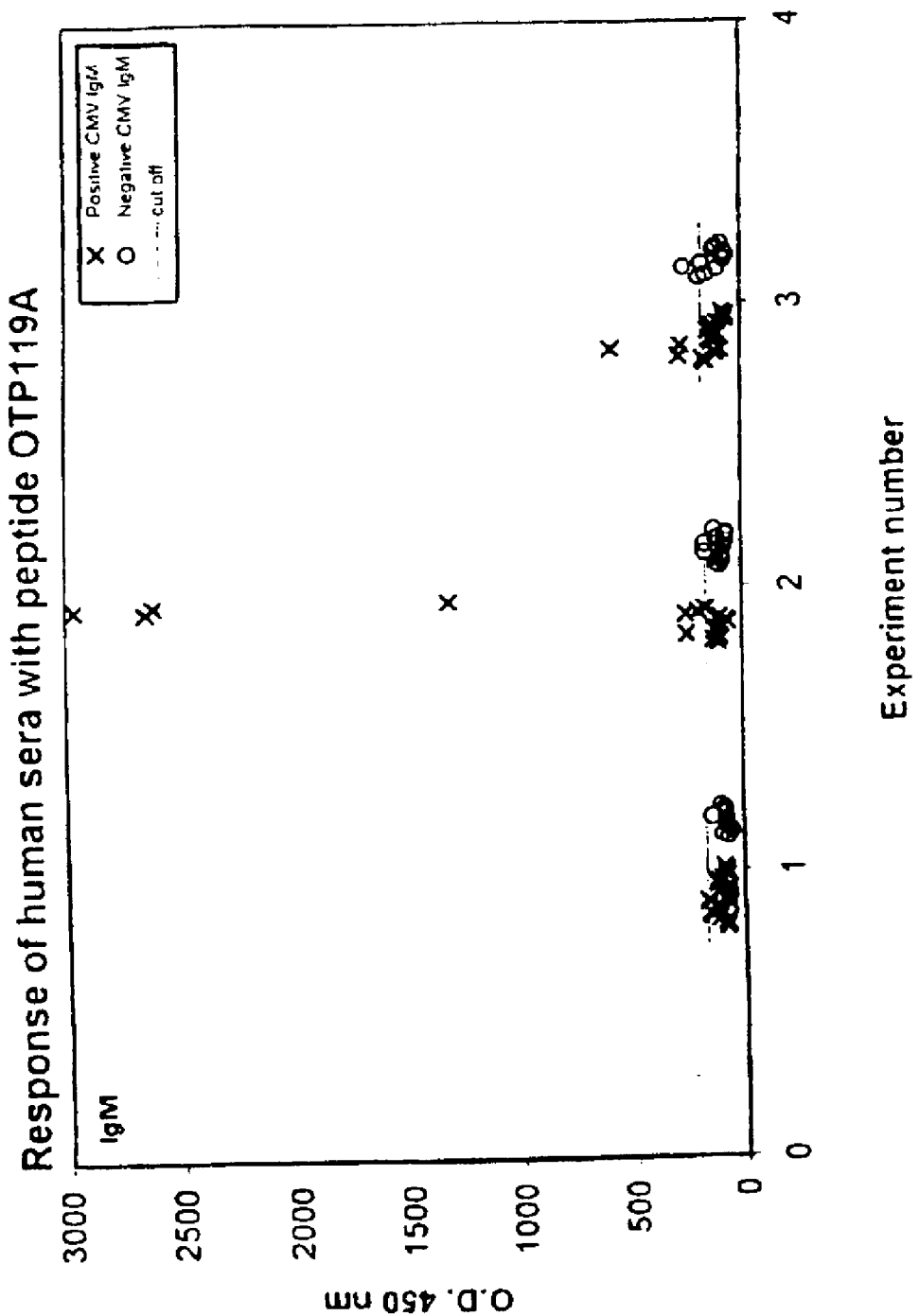

The result of such a PEPSCAN analysis with 10 sera from different CMV-seropositive individuals is shown in FIG. 1.

Panel A shows the relative absorbance values for each individual serum tested.

Panel B shows the sum of individual absorbance values for each peptide, corrected for the background value for each serum.

Panel C shows the positivity-score for each peptide yielding an absorbence value of at least 3 SD above the mean background value for each serum tested.

The background absorbance value for each serum was determined as the mean absorbance value of the 10 least reactive peptides.

From this figure it can be seen that most sera contain antibodies reactive with distinct regions of the pp28 amino acid sequence. Some regions are recognized by multiple individuals, thus representing immunodominant epitopes of pp28.

Similar date have been obtained by PEPSCAN analysis of other CMV proteins such as pp150(UL32), pp65(UL83), pp52(UL44).

Conclusion: Antibodies in the sera from different individuals recognize CMV proteins through interaction with distinct regions (epitope clusters), the position of which may differ significantly for each individual.

EXAMPLE 2

Selected peptides of different length (see sequence listing) were synthesized using standard solid phase synthesis to combine multiple PEPSCAN reactive domains into a single molecule.

These peptides were coated onto the solid phase in the wells of 96-well micro-ELISA plates, usually at 1 µg/ml in coating buffer and non-bound positions were blocked with 1% bovine serum albumine (BSA) in coating buffer. Peptides were coated directly or as BSA-peptide complexes created by glutaraldehyde mediated coupling of peptides to highly purified BSA, depending to the best immunochemical reactivity as determined in optimization experiments.

After coating, the wells were washed with 0.1M phosphate buffered saline pH7.4 (PBS) containing 0.05% Tween-20 (PBS-T) and dilutions of human sera in PBS-T (usually 1:100) were analyzed for antibody reactivity using standard ELISA procedures.

In FIG. 2 the peptide ELISA results are shown for IgG antibodies using sera from random healthy individuals seropositive or seronegative for CMV antibodies as determined by reference antibody assays.

In the following table, for each panel is the corresponding peptide analysis is shown:

Panel 2A—peptide #T21C (SEQ.ID.No. 2),
Panel 2B—peptide #C21M (SEQ.ID.No. 3),
Panel 2C—peptide #T21CC21M (SEQ.ID.No. 4),
Panel 2D—peptide #K38E (SEQ.ID.No. 1),
Panel 2E—peptide #OTP194 (SEQ.ID.No. 5),
Panel 2F—peptide #OTP197 (SEQ.ID.No. 6),
Panel 2G—peptide #F28G (SEQ.ID.No. 8),
Panel 2H—peptide #OTP101A (SEQ.ID.No. 7),
Panel 2I—peptide #OTP118A (SEQ.ID.No. 9),
Panel 2J—peptide #OTP119A (SEQ.ID.No. 10),
Panel 2K—CMV-Ag being the cell culture extract (golden standard).

In each panel 4 such experiments are shown with different sets of human sera obtained from random healthy blood donors.

The CMV immune status was determined using a reference "golden standard" (*) ELISA based upon cell culture derived CMV antigens (Panel 2K).

(o) represents CMV seropositive samples (x) represents CMV seronegative samples.

(*) Antigens for the "golden standard" consisted of purified de-enveloped virions and dense bodies, prepared from human embryonic lung fibroblasts, infected for 6 days with 3PFU/cell of CMV strain AD-169. Infected cells were freeze-thawed 3 times and extracted with 0.35% TX100 in 0.05M phosphate buffer pH7.4 to release intracellular virions and dense bodies into the soluble phase. Soluble particles were separated from nuclei and larger cellular material by density centrifugation over a Ficoll layer for 20 min. at 1200×g at +4° C. From the upper layer viral particles were isolated by centrifugation at 12.000×g for 10 minutes and the pelleted particles were solubilised by short sonication in PBS. By electron microscopy the particles were shown to consist predominantly of de-enveloped viral capsids and dense bodies.

In FIG. 3 a selection of the results is shown of analyses representing the best set of peptides reacting with IgM antibodies using sera from patients with active CMV-infections and appropriate controls without active CMV-infections.

Sera were obtained from renal transplant patients with active CMV infections, showing a positive reaction for CMV-IgM in the reference ELISA.

In the following table, for each panel is the corresponding peptide analysis is shown:

Panel 3A—peptide #K38E (SEQ ID No.1),
Panel 3B—peptide #K21CC21M (SEQ ID No. 4),
Panel 3C—peptide #F28G (SEQ ID No.8),
Panel 3D—peptide #OTP119A (SEQ ID No.10).

Conclusion: The data shown in FIGS. 2 and 3 indicate that individual combi-peptides are reactive with antibodies in most human sera but that no peptide shows reactivity with all sera. Occasionally some peptides react (false-positive) with CMV-negative sera.

Therefore, although most selected peptides appear to be reactive with several human sera no single peptide is reactive with all sera.

EXAMPLE 3

In several experiments performed it was found that selected combination(s) of well defined synthetic combi-peptides derived from different immunoreactive CMV-proteins, especially the combination of [#K38E+#OTP101A+#OTP119A](SEQ.ID.No. 1 SEQ.ID.No. 7+SEQ.ID.No. 10), were capable of detecting CMV-IgG antibodies in human sera with equal or better sensitivity than current "golden standard" ELISA using CMV antigens derived from cell culture.

CMV-Ag was prepared and coated on the solid phase as described in Example 2. #OTP101A (SEQ.ID.No. 7) was coupled to BSA before coating in equimolar ratio with #K38E (SEQ.ID.No. 1) and #OTP119A (SEQ.ID.No. 10).

Figure 4A:
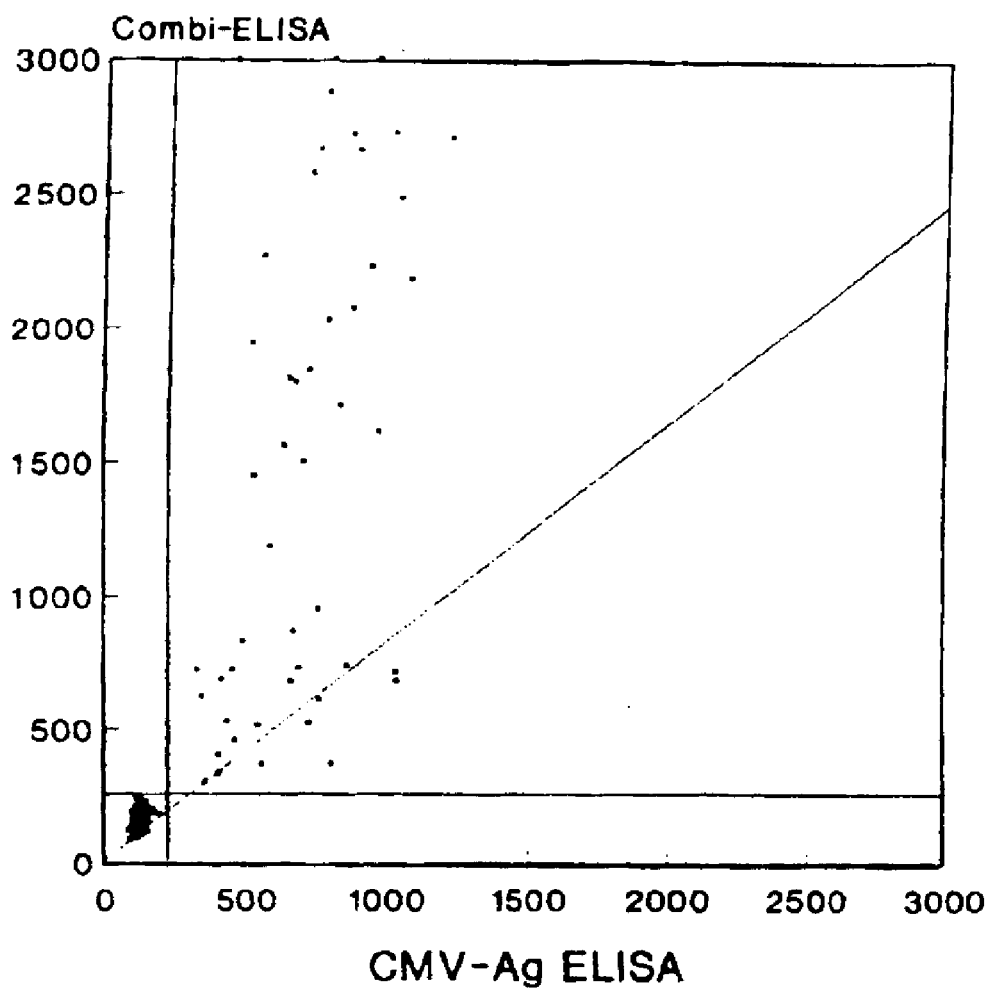
Figure 4B:
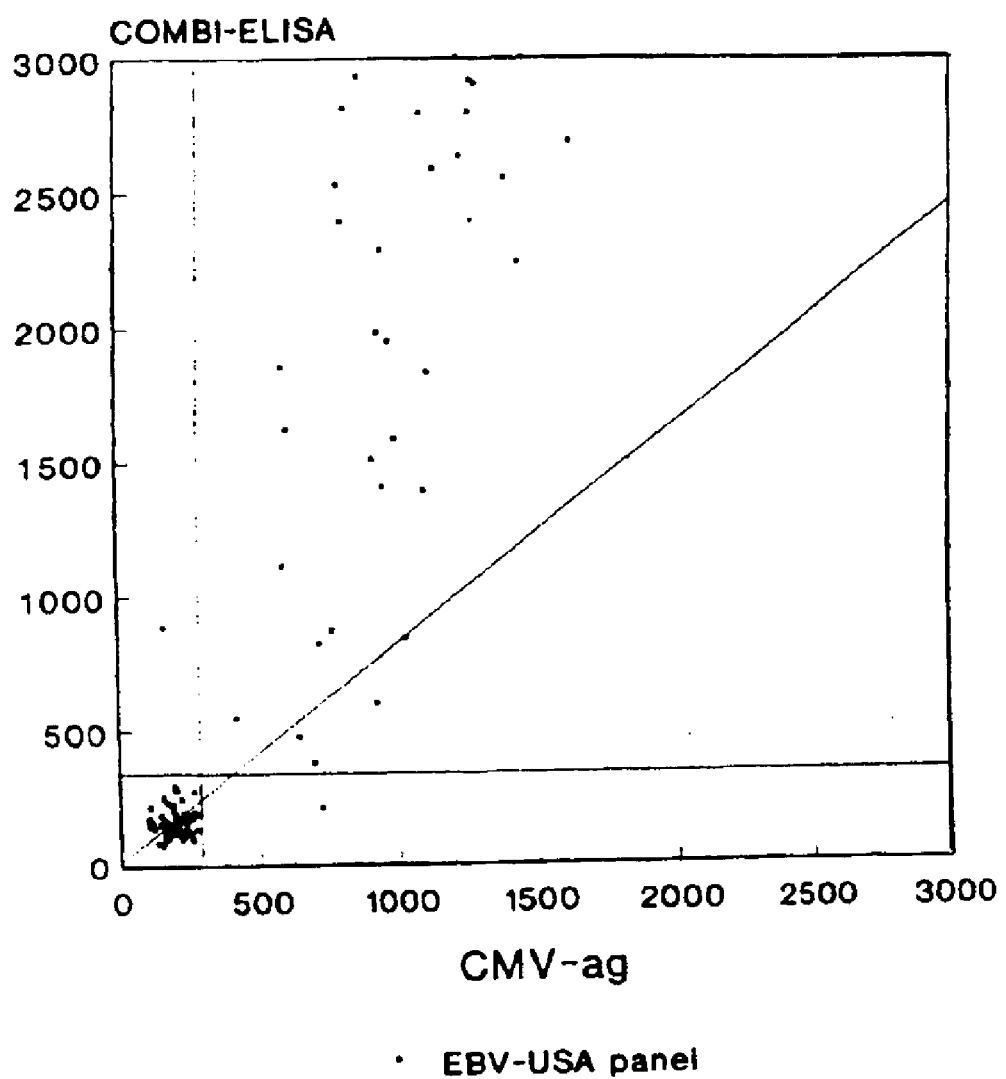

In FIG. 4 data is shown wherein CMV-IgG reactivity in a peptide combination ELISA is compared with the reference ELISA which uses semi-purified cell culture derived CMV antigen on the solid phase. The sera analysed were from healthy blood donors either from the USA (4A) or from The Netherlands (4B).

The CMV-IgG reactivity as determined in the peptide-based ELISA (vertical axis) gives equal or even better reactivities compared to the "golden standard" ELISA (horizontal axis). Control human sera, negative for CMV-IgG are negative in both assays.

The presence of all three peptides on the solid phase was checked using epitope-specific antibodies (data not shown).

Conclusion: The availability of such a well specified set of CMV synthetic molecules is of value for the development of highly defined assays for the detection of anti-CMV, IgG in human sera and may contribute to further standardization of CMV-serodiagnosis and determination of CMV-immune status.

EXAMPLE 4

Combination of multiple selected combi-peptides in a single well was also necessary to obtain sufficient reactivity with human anti-CMV IgM as no single peptide was capable of reacting to a similar extend as cell culture CMV-Ag with all sera that were analysed (Example 2).

Therefore several combinations of peptides were tested and optimized.

From these results the best combination of peptides for the detection of human serum anti-CMV IgM proved to be [#K38E+#F28G] (SEQ.ID.No. 1+SEQ.ID.No. 8).

Figure 5:
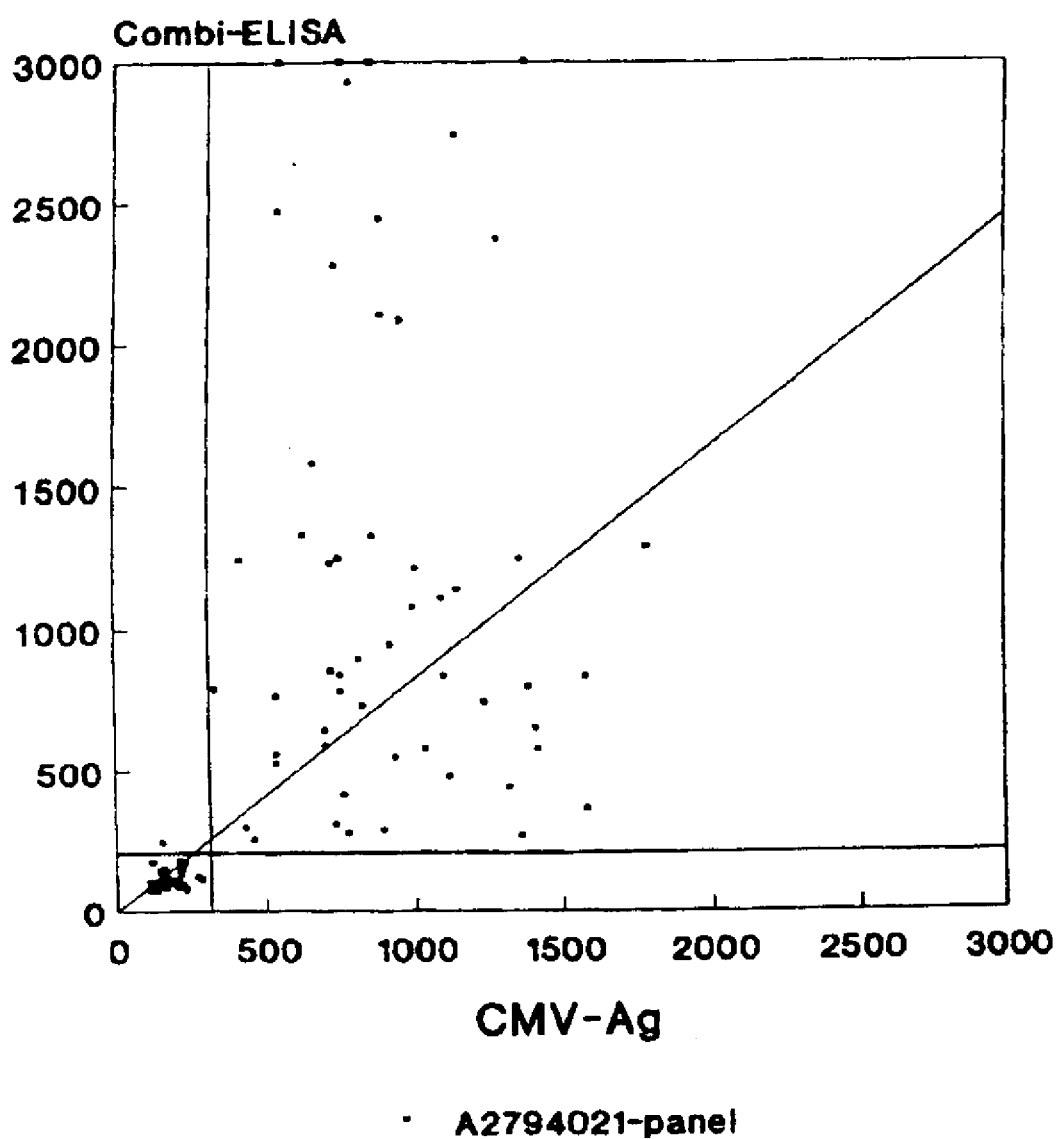

FIG. 5 shows the comparison of the reactivity of human serum IgM with cell culture derived CMV-Ag and [#K38E+#F28G] (SEQ.ID.No. 1+SEQ.ID.No. 8) bound to the solid phase at 1 µg/ml.

Sera were obtained from renal transplant patients with a well, defined primary CMV-infection.

CMV-Ag were prepared and coated as described in Example 2 and peptides were coated simultaneously onto the solid phase each at 1 µg/ml in 0.05M carbonate buffer pH9.6.

It can be concluded that [#K38E+#F28G] (SEQ.ID.No. 1+SEQ.ID.No. 8) provides an excellent and well defined combination capable of replacing cell culture derived CMV-Ag in the detection of human anti-CMV-IgM antibodies.

EXAMPLE 5

Monoclonal antibodies reactive with CMV-peptide reagents according to the present invention are useful for diagnostic assays (e.g. as CMV-specific conjugate in IgM-capture assays, as quality control to determine peptide coating on solid phase).

Such antibodies may also be useful in the direct detection of CMV in cultured cells and patient tissue or body fluids.

For illustration only one of such an antibody, named CMV.OT3C (deposited at the European Collection of Animal Cell Cultures, CAMR (Centre for Applied Microbiology & Research), Salisbury (UK) under deposit No. 96071123) directed against the C-terminal domain of CMV-pp150 (UL32) and reactive with peptide #K38E (SEQ.ID.No. 1) by ELISA, is described. The antibody is capable of detecting intact pp150 in CMV-infected cell lysates by ELISA, immunoblot or immunoprecipitation and specifically stains CMV-infected cells by immunofluorescence or immunohistochemical techniques.

Direct enzyme coupling of CMV.OT3C yields an antibody conjugate which may be employed as CMV-specific detector reagent in (IgM or IgA) immunocapture assays.

Figure 6:
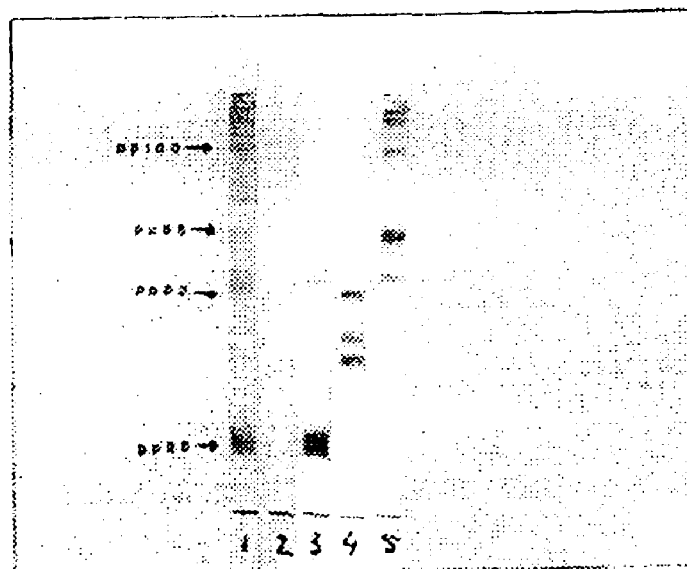

In FIG. 6, an immunoblot is shown which was prepared as follow: Proteins of CMV-AD169 infected human fibroblast whole cell lysate were denatured and separated by standard Laemmli SDS-PAGE and blotted onto nitrocellulose. Strips were cut and remaining protein binding sites were blocked by incubation for one hour with 4% dry milk powder dissolved in PBS with 5% horse serum(blocking buffer). Subsequently the strips were incubated with monoclonal antibody in blocking buffer for one hour at 37° C. After washing with PBS-Tween anti-mouse HRP conjugate was added and incubated as above and bound enzyme reactivity was detected using 4-chloronaphtol as precipitating substrate.

Control reactions with monoclonal antibodies to additional CMV proteins (GICR series obtained from Goodwin Institute for Cancer Research, Florida, USA) and human serum IgG from a CMV-seropositive donor are shown in the parallel strips as indicated in the legend below the figure.

What is claimed is:

1. An isolated peptide reagent, comprising a first peptide comprising the amino acid sequence of SEQ ID NO:1, a second peptide comprising the amino acid sequence of SEQ ID NO:7 and a third peptide comprising the amino acid sequence of SEQ ID NO:10.

2. A peptide reagent, consisting of a first peptide consisting of the amino acid sequence of SEQ ID NO:1, a second, separate peptide consisting of the amino acid sequence of SEQ ID NO:7, and a third, separate peptide consisting of the amino acid sequence of SEQ ID NO:10.

3. A method for the detection of antibodies to CMV in a sample, comprising contacting the peptide reagent of claim 1 with the sample under conditions whereby an antigen/antibody complex can form and detecting formation of an antigen/antibody complex, thereby detecting antibodies to CMV in the sample.

4. A method for the detection of antibodies to CMV in a sample, comprising contacting the peptide reagent of claim 2 with the sample under conditions whereby an antigen/antibody complex can form and detecting formation of an antigen/antibody complex, thereby detecting antibodies to CMV in the sample.

5. A test kit comprising the peptide reagent of claim 1.

6. A test kit comprising the peptide reagent of claim 2.

* * * * *

UNITED STATES PATENT AND TRADEMARK OFFICE
CERTIFICATE OF CORRECTION

PATENT NO. : 6,936,251 B2
DATED : August 30, 2005
INVENTOR(S) : Middeldorp et al.

It is certified that error appears in the above-identified patent and that said Letters Patent is hereby corrected as shown below:

<u>Title page</u>,
Item [73], Assignee, should read -- bioMerieux, B.V., Boxtel (NL) --.
Item [56], References Cited, FOREIGN PATENT DOCUMENTS, should include
-- WO    WO 96/01321    1/1996 --.

Signed and Sealed this

Eleventh Day of April, 2006

JON W. DUDAS
*Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 38 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Cytomegalovirus (xi) SEQUENCE DESCRIPTION: SEQ ID NO: 1:

```
Lys Ser Gly Thr Gly Pro Gln Pro Gly Ser Ala Gly Met Gly Gly Ala
 1               5                  10                  15

Lys Thr Pro Ser Asp Ala Val Gln Asn Ile Leu Gln Lys Ile Glu Lys
                20                  25                  30

Ile Lys Asn Thr Glu Glu
                35
```

(2) INFORMATION FOR SEQ ID NO: 2:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Cytomegalovirus (xi) SEQUENCE DESCRIPTION: SEQ ID NO: 2:

```
Thr Pro Thr Pro Val Asn Pro Ser Thr Ala Pro Ala Pro Ala Pro Thr
 1               5                  10                  15

Pro Thr Phe Ala Cys
                20
```

(2) INFORMATION FOR SEQ ID NO: 3:

(i) SEQUENCE CHARACTERISTICS:
      (A) LENGTH: 21 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: Cytomegalovirus (xi) SEQUENCE DESCRIPTION: SEQ ID NO: 3:

```
Cys Gln Thr Pro Val Asn Gly Asn Ser Pro Trp Ala Pro Thr Ala Pro
 1               5                  10                  15

Leu Pro Gly Asp Met
                20
```

(2) INFORMATION FOR SEQ ID NO: 4:

(i) SEQUENCE CHARACTERISTICS:
    (A) LENGTH: 42 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Cytomegalovirus (xi) SEQUENCE DESCRIPTION: SEQ ID NO: 4:

```
Thr Pro Thr Pro Val Asn Pro Ser Thr Ala Pro Ala Pro Ala Pro Thr
1               5                  10                  15

Pro Thr Phe Ala Cys Cys Gln Thr Pro Val Asn Gly Asn Ser Pro Trp
            20                  25                  30

Ala Pro Thr Ala Pro Leu Pro Gly Asp Met
            35                  40
```

(2) INFORMATION FOR SEQ ID NO: 5:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cytomegalovirus (xi) SEQUENCE DESCRIPTION: SEQ ID NO: 5:

```
Thr Asp Thr Glu Thr Ser Ala Lys Pro Pro Val Thr Thr Ala Tyr Lys
1               5                  10                  15

Phe Glu Gln Pro Thr Leu Thr Phe Gly Ala Gly Val Asn
            20                  25
```

(2) INFORMATION FOR SEQ ID NO: 6:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cytomegalovirus (xi) SEQUENCE DESCRIPTION: SEQ ID NO: 6:

```
Asp Gly Tyr Pro Pro Asn Arg Gln Asp Pro Arg Phe Thr Asp Thr Leu
1               5                  10                  15

Val Asp Ile Thr Asp Thr Glu Thr Ser Ala Lys
            20                  25
```

(2) INFORMATION FOR SEQ ID NO: 7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cytomegalovirus (xi) SEQUENCE DESCRIPTION: SEQ ID NO: 7:

Ser Glu Ala Val Ser His Arg Ala Asn Glu Thr Ile Tyr Asn Thr Thr
1               5                   10                  15

Leu Lys Tyr Gly Asp Val
            20

(2) INFORMATION FOR SEQ ID NO: 8:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cytomegalovirus (xi) SEQUENCE DESCRIPTION: SEQ ID NO: 8:

Phe Leu Thr Glu Glu Pro Phe Gln Arg Gly Asp Pro Phe Asp Lys Asn
1               5                   10                  15

Tyr Val Gly Asn Ser Gly Lys Ser Arg Gly Gly Gly
            20                  25

(2) INFORMATION FOR SEQ ID NO: 9:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cytomegalovirus (xi) SEQUENCE DESCRIPTION: SEQ ID NO: 9:

Thr Thr Pro Gly Glu Pro Leu Lys Asp Ala Leu Gly Arg Gln Val Ser
1               5                   10                  15

Leu Arg Ser Tyr Asp Asn Ile Pro Pro Thr Ser Ser Ser Asp Glu Gly
            20                  25                  30

Glu Asp Asp Asp Cys
            35

(2) INFORMATION FOR SEQ ID NO: 10:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Cytomegalovirus (xi) SEQUENCE DESCRIPTION: SEQ ID NO: 10:

Cys Glu Thr Asp Asp Leu Asp Glu Glu Asp Thr Ser Ile Tyr Leu Ser
1               5                   10                  15

-continued

```
Pro Pro Pro Val Pro Pro Val Gln Val Val Ala Lys Arg Leu Pro Arg
            20              25              30
Pro Asp Thr Pro Arg Thr
        35
```